(12) United States Patent
Llenas Calvo et al.

(10) Patent No.: US 11,242,312 B2
(45) Date of Patent: Feb. 8, 2022

(54) DIPEPTIDYL KETOAMIDE META-METHOXYPHENYL DERIVATIVES AND USES THEREOF

(71) Applicant: LANDSTEINER GENMED, S.L., Seville (ES)

(72) Inventors: Jesús Llenas Calvo, Seville (ES); Miriam Royo Expósito, Barcelona (ES); Unai Elezcano Donaire, Barcelona (ES); Enrique Vázquez Tatay, Seville (ES); Marta Melgarejo Díaz, Barcelona (ES); Marta Isabel Barranco Gallardo, Barcelona (ES); Eva Mª Medina Fuentes, Barcelona (ES)

(73) Assignee: LANDSTEINER GENMED, S.L., Seville (ES)

( * ) Notice: Subject to any disclaimer, the term of this patent is extended or adjusted under 35 U.S.C. 154(b) by 0 days.

(21) Appl. No.: 17/051,896

(22) PCT Filed: May 3, 2019

(86) PCT No.: PCT/EP2019/061369
§ 371 (c)(1),
(2) Date: Oct. 30, 2020

(87) PCT Pub. No.: WO2019/211434
PCT Pub. Date: Nov. 7, 2019

(65) Prior Publication Data
US 2021/0317075 A1  Oct. 14, 2021

(30) Foreign Application Priority Data
May 3, 2018 (EP) ..................... 18382306

(51) Int. Cl.
*C07C 235/84* (2006.01)
*C07K 5/02* (2006.01)
*C07C 237/22* (2006.01)
*C07C 259/06* (2006.01)

(52) U.S. Cl.
CPC .......... *C07C 235/84* (2013.01); *C07C 237/22* (2013.01); *C07C 259/06* (2013.01); *C07K 5/02* (2013.01)

(58) Field of Classification Search
None
See application file for complete search history.

(56) References Cited

U.S. PATENT DOCUMENTS

| 7,491,705 B2 | 2/2009 | Shirasaki et al. |
| 10,294,269 B2 | 5/2019 | Llenas Calvo et al. |
| 2006/0258598 A1 | 11/2006 | Herzner et al. |

FOREIGN PATENT DOCUMENTS

| WO | 2004078908 A2 | 9/2004 |
| WO | 2005056519 A1 | 6/2005 |
| WO | 2016038040 A2 | 3/2016 |
| WO | 2017156074 A1 | 9/2017 |

OTHER PUBLICATIONS

Lescop et al., "Novel cell-penetrating alpha-keto-amide calpain inhibitors as potential treatment for muscular dystrophy," Bioorg. Med. Chem. Lett., 2005, vol. 15, pp. 5176-5181.
M.E. Saez et al.; "The therapeutic potential of the calpain family: new aspects," Drug Discovery Today 2006, vol. 11, pp. 917-923.
Y. Huang et al., "The calpain family and human disease," Trends in Molecular Medicine. 2001 vol. 7, pp. 355-362.
IM Medana et al., "Cerebral calpain in fatal falciparum malaria," Neuropath and Appl. Neurobiol. 2007, vol. 33, pp. 179-192.
Yoshida, Ken Ischi et al., "Calpain is Implicated in Rat Myocardial Injury after Ischemia or Reperfusion," Jap. Circ. J. 1995, vol. 59, pp. 40-48.
Ye et al., "Over-Expression of Calpastatin Inhibits Calpain Activation and Attenuates Post-Infarction Myocardial Remodeling," PLoS ONE, 2015, vol. 10, e0120178, doi:10/1371/journal.pone.0120178.
Kudo-Sakamoto et al., "Calpain-dependent Cleavage of N-cadherin Is Involved in the Progression of Post-myocardial Infarction Remodeling," Journal Biological Chemistry, 2014, vol. 289, pp. 19408-19419.
Neuhof et al., "Calpain system and its involvement in myocardial ischemia and reperfusion injury," World J Cardiol, 2014, vol. 6, pp. 638-652.
Poncelas et al., "Delayed, oral pharmacological inhibition of calpains attenuates adverse post-infarction remodelling," Cardiovascular Research, 2017, vol. 113, pp. 950-961.
Seung-Chyul Hong et al., "Neuroprotection With a Calpain Inhibitor in a Model of Focal Cerebral Ischemia," Stroke 1994, vol. 25, pp. 663-669.
R. T. Bartus et al., "Calpain as a novel target for treating acute neurodegeneratie disorders," Neurological Res. 1995, vol. 17, pp. 249-258.
K. E. Saatman et al., "Calpain inhibitor AK295 attenuates motor and cognitive deficits following experimental brain injury in the rat," Proc. Natl. Acad. Sci. USA, 1996, vol. 93, pp. 3428-3433.
C. L. Edelstein et al., "The role of cysteine proteases in hypoxia-induced rat renal proximal tubular injury," Proc. Natl. Acad. Sci. USA, 1995, vol. 92, pp. 7662-7666.
J. Peltier et al., "Calpain Activation and Secretion Promote Glomerular Injury in Experimental Glomerulonephritis: Evidence from Calpastatin-Transgenic Mice," J Amer Soc Nephrol. 2006, vol. 17, pp. 3415-3423.
Groshong JS et al., "Calpain activation impairs neuromuscular transmission in a mouse model of the slow-channel myasthenic syndrome," J Clin Invest 2007, vol. 117, pp. 2903-2912.

(Continued)

*Primary Examiner* — Amy C Bonaparte
(74) *Attorney, Agent, or Firm* — Tristan A. Fuierer; Olive Law Group, PLLC

(57) ABSTRACT

The present invention relates to dipeptidyl ketoamide m-methoxyphenyl derivatives and their use in the treatment of diseases and conditions associated with elevated calpain activity, such as heart injury caused by infarction, ischemia with or without reperfusion, neurodegenerative disorders, malaria, diabetic nephropathy, neurotoxicity induced by HIV virus, cancer, and fibrotic diseases.

20 Claims, No Drawings

(56) References Cited

OTHER PUBLICATIONS

J Takano et al., "Calpain Mediates Excitotoxic DNA Fragmentation via Mitochondrial Pathways in Adult Brains," J Biol Chem. 2005, vol. 280, pp. 16175-16184.
M J Spencer et al., "Overexpession of a calpastatin transgene in mdx muscle reduces dystrophic pathology," Hum Mol Gen, 2002, vol. 11, pp. 2645-2655.
Nixon R.A., "The calpains in aging and aging-related diseases," Ageing Res Rev. Oct. 2003; vol. 2, pp. 407-418.
Saito K, et al., "Widespread activation of calcium-activated neutral proteinase (calpain) in the brain in Alzheimer disease: A potential molecular basis for neuronal degeneration," Proc Natl Acad Sci USA. Apr. 1, 1993; vol. 90, pp. 2628-2632.
Wang KK, "Calpain and caspase: can you tell the difference?" Trends Neurosci. Jan. 2000; vol. 23, pp. 20-26.
Siman R. et al., "Proteolytic Processing of Beta-Amyloid Precursor by Calpain I," J Neurosci. Jul. 1990; vol. 10, pp. 2400-2411.
Wang KK et al., "Development and Therapeutic Potential of Calpain Inhibitors," Adv Pharmacol. 1997; vol. 37, pp. 117-152.
Banno Y. et al., "Endogenous Cleavage of Phospholipase C-Beta3 by Agonist-induced Activation of Calpain in Human Platelets," J Biol Chem. Mar. 3, 1995; vol. 270, pp. 4318-4324.
Lee MS . et al., "Neurotoxicity induces cleavage of p35 to p25by calpain," Nature. May 18, 2000; vol. 405, pp. 360-364.
Carillo S, et al. "Defferential sensitivity of FOS and JUN family members to calpains", Oncogene. Jun. 1994; vol. 9, pp. 1679-1689.
Lin YC,e t al., "Activation of NF-κB requires proteolysis of the inhibitor IκB-alpha: Signal-induced phosphorylation of IκB-alpha alone does not release active NF-κB, "Proc Natl Acad Sci U S A., Jan. 17, 1995; vol. 92(2):pp. 552-556.
Mbebi C, et al.; "Amyloid Precursor Protein Family-induced Neuronal Death Is Mediated by Impairment of the Neuroprotective Calcium/Calmodulin Protein Kinase IV-dependent Signaling Pathway," J Biol Chem., Jun. 7, 2002; vol. 277(23): pp. 20979-20990.
Sant'Angelo A, et al.; "Usefulness of Behavioral and Electrophysiological Studies in Transgenic Models of Alzheimer's Disease," Neurochem Res., Jul. 2003; vol. 28(7): pp. 1009-1015.
Bliss TV. et al, "A Synaptic Model of Memory: long-term potentiation in the hippocampus," Collingridge GL Nature, Jan. 7, 1993; vol. 361(6407): pp. 31-39.
K.K.W. Wang et al., "Calpain inhibition: an overview of its therapeutic potential," Trends in Pharmacol. Sci., 1994,15, 412-419.
Higuchi et al.; "Distinct Mechanistic Roles of Calpain and Caspase Activation in Neurodegeneration as Revealed in Mice Overexpressing Their Specific Inhibitors," J. Biol. Chem. 2005, vol. 280 (15), pp. 15229-15237.
Hassen GW et al.; "A novel calpain inhibitor for the treatment of acute experimental autoimmune encephalomyelitis," J. Neuroimmunology 2006, vol. 180, pp. 135-146.
Park et al.; The Generation of a 17 kDa Neurotoxic Fragment: An Alternative Mechanism by which Tau Mediates β-Amyloid-Induced NeurodegenerationJ. Neurosci. 2005, 25, pp. 5365-5375.
J. Higaki et al., "Inhibition of-Amyloid Formation Identifies Proteolytic Precursors and SubceUular Site of Catabolism," Neuron, 1995, vol. 14, pp. 651-659.
O'Donnell et al.; "Human Immunodeficiency Virus (HIV)-Induced Neurotoxicity: Roles for the NMDA Receptor Subtypes 2A and 2B and the Calcium-Activated Protease Calpain by a CSF-derived HIV-1 Strain," J. Neurosci., 2006, vol. 26 (3), pp. 981-990.
Teranishi et al.; "Calpain is involved in the HIV replication from the latently infected OM10.1 cells," Biochem. Biophys. Res. Comm. 2003, vol. 303 (3), pp. 940-946.
Y. Shi et al., "Downregulation of the calpain inhibitor protein calpastatin by caspases during renal ischemia-reperfusion," Am. J. Physiol. Renal Physiol., 2000, vol. 279, pp. F509-F517.
A Dnyanmote et al., Calpastatin overexpression prevents progression of S-1,2-dichlorovinyl-L-cysteine (DCVC)-initiated acute renal injury and renal failure (ARF) in diabetesToxicology and Applied Pharmacology, 2006, vol. 215, pp. 146-157.
P. Chatterjee et al., "Inhibitors of calpain activation (PD150606 and E-64) and renal ischemia-reperfusion injury," Biochem. Pharmacol. 2005, vol. 7, pp. 1121-1131.
D. Greenbaum et al., "Apicomplexan Parasites Co-Opt Host Calpains to Facilitate Their Escape from Infected Cells," Science. May 8, 2009; 324(5928): 794-797. doi:10.1126/science.1171085.
Li et al., "BDA-410: A novel synthetic calpain inhibitor active against blood stage malaria," Mol Biochem Parasitol. 2007; vol. 155(1): pp. 26-32.
Jung et al. "Antimalarial Effect of N-acetyl-L-Leucyl-L-leucyl-L-norieucinal by the Inhibition of Plasmodium falciparum Calpain," Archives of Pharmacal Research (2009), vol. 32(6), pp. 899-906.
Chandramohanadas et al. "Apicomplexan Parasites Co-Opt Host Calpains to Facilitate Their Escape from Infected Cells," Science. May 8, 2009; 324(5928): 794-797. doi:10.1126/science.1171085, duplicate of #40.
Leloup et al.; Calpains as potential anti-cancer targets, Expert Opin Ther Targets., 2011, vol. 15(3), pp. 309-323.
Storr et al., "The calpain system and cancer," Nat Rev Cancer., 2011, vol. 11(5), pp. 364-374.
Storr et al., "Calpain in Breast Cancer: Role in Disease Progression and Treatment Response," Pathobiology, 2015, vol. 82(3-4), pp. 133-141.
Selvakumar et al., "Involvement of calpain in colorectal adenocarcinomas (Review)," Experimental Therapeutic Medicine, 2010, vol. 1, pp. 413-417.
Storr et al., The calpain system is associated with survival of breast cancer patients with large but operable inflammatory and noninflammatory tumours treated with neoadjuvant chemotherapy, Oncotarget, 2016, vol. 30(7), pp. 47927-47937.
Guan et al., "Apoptosis induced by calpain inhibitors in leukemia cells and HeLa cells," Proc Amer Assoc Cancer Res., 2005, vol. 46, Abstract Only.
Friedman et al. ,"Therapy for Fibrotic Diseases: Nearing the Starting Line," Sci. Transl. Med. 5, 167sr1 (2013).
Nassar et al., "Calpain Activity Is Essential in Skin Wound Healing and Contributes to Scar Formation," PLoS ONE, 2012, 7(5), e37084.
Buckman et al., "Calpain Inhibition as Anti-Fibrotic Therapy: Discovery and Pre-Clinical Evaluation of Novel Inhibitors of Models of Lung and Liver Fibrosis,"Am J Respir Crit Care Med, 2018, vol. 197, A5747, Abstract Only.
Potz et al., "Role of Calpain in Pathogenesis of Human Disease Processes," J Nat Sci 2016, vol. 2(9), e218.
Ono et al., "Calpain research for drug discovery: challenges and potential," Nature Reviews Drug Discovery, 2016, vol. 15, pp. 854-876.
Trager N. et al., "Effects of a Novel Orally Administered Calpain Inhibitor SNJ-1945 on Immunomodulation and Neurodegeneration in a Murine Model of Multiple Sclerosis," J. Neurochem., Jul. 2014; vol. 130(2): pp. 268-279.

DIPEPTIDYL KETOAMIDE META-METHOXYPHENYL DERIVATIVES AND USES THEREOF

CROSS-REFERENCE TO RELATED APPLICATIONS

This application is filed under the provisions of 35 U.S.C. § 371 and claims the priority of International Patent Application No. PCT/EP2019/061369 filed on 3 May 2019 entitled "DIPEPTIDYL KETOAMIDE META-METHOXYPHENYL DERIVATIVES AND USES THEREOF" in the name of Jesús LLENAS CALVO, et al., which claims priority to European Patent Application No. 18382306.1, filed on 3 May 2018, both of which are hereby incorporated by reference herein in their entirety.

FIELD OF THE INVENTION

The invention relates to dipeptidyl ketoamide m-methoxyphenyl derivatives and their use in the treatment of diseases and conditions associated with elevated calpain activity, such as heart injury caused by infarction, ischemia with or without reperfusion, neurodegenerative disorders, malaria, diabetic nephropathy, neurotoxicity induced by HIV virus, cancer, and fibrotic diseases.

BACKGROUND OF THE INVENTION

Calpains are intracellular proteins belonging to the family of calcium-dependent, non-lysosomal cysteine proteases (proteolytic enzymes) expressed ubiquitously in mammals and many other organisms. Two major forms, calpain 1 and calpain 2, also known as µ-calpain and m-calpain, have been described but further calpain isoenzymes are also postulated (M. E. Saez et al.; Drug Discovery Today 2006, 11 (19/20), pp. 917-923). 20 Calpains play an important role in various physiological processes which include the cleavage of different regulatory proteins (K. K. Wang et al., Trends in Pharmacol. Sci. 1994, 15, pp. 412-419).

Elevated calpain levels have been measured in various pathophysiological processes, for example: ischemias of the heart, the kidney, the lung, the liver or the central nervous system, inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above) and infectious diseases such as malaria (IM Medana et al., Neuropath and Appl. Neurobiol. 2007, 33, pp. 179-192). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes. For this reason, it was postulated that inhibitors of calpain could be of use for treating these diseases.

Yoshida, Ken Ischi et al. (Jap. Circ. J. 1995, 59 (1), pp. 40-48), taught that calpain inhibitors had favorable effects following cardiac damage produced by ischemia or reperfusion. Recently, it has been disclosed that calpains activate during myocardial ischemia-reperfusion and contribute to reperfusion injury, as well as the involvement of calpains in post-infarction remodeling and heart failure. After an acute myocardial infarction, the global heart undergoes a series of structural changes, termed post-infarction myocardial remodeling, leading to the incidence of heart failure. Ventricular remodeling includes the dilatation, hypertrophy, and the formation of a discrete collagen scar. The dysregulation of calpain activity plays an important role in reperfusion injury and myocardial remodeling, suggesting that inhibition of calpain is a potential therapeutic strategy (Ye et al., PLoS ONE, 2015, 10(3), e0120178; Kudo-Sakamoto et al., Journal Biological Chemistry, 2014, 289(28), pp. 19408-19419). Calpain inhibitors have been reported by Neuhof et al. (World J Cardiol, 2014, 6(7), 638-652) as a new prophylactic and therapeutic possibility for patients with myocardial infarction, revascularization and coronary surgery. The study reported by Poncelas et al. (Cardiovascular Research, 2017, 113(8), pp. 950-961) confirm this role of calpains and show that sustained pharmacological inhibitor of calpains is a promising therapeutic strategy against adverse post-infraction remodeling Calpain inhibitors have also been shown to provide a neuroprotective effect in acute neurodegenerative impairments or ischemias such as occur after cerebral stroke (Seung-Chyul Hong et al., Stroke 1994, 25 (3), pp. 663-669, and R. T. Bartus et al., Neurological Res. 1995, 17, pp. 249-258).

It has also been shown that following experimental brain trauma, calpain inhibitors improve recovery from the memory performance deficits and neuromotor impairments (K. E. Saatman et al., Proc. Natl. Acad. Sci. USA, 1996, 93, pp. 3428-3433) and that calpain inhibitors have a protective effect on hypoxia-damaged kidneys (C. L. Edelstein et al., Proc. Natl. Acad. Sci. USA, 1995, 92, pp. 7662-6).

More recent studies have shown that calpastatin (the natural inhibitor of calpain) significantly attenuates the pathophysiological effects of activated calpain in a number of diseases such as a) experimental glomerulonephritis (J. Peltier et al., J A, Soc Nephrol. 2006, 17, pp. 3415-3423), b) in cardiovascular remodelling in angiotensin II-induced hypertension, c) impaired synaptic transmission in slow-channel congenital myasthenic syndrome (Groshong J S et al., J Clin Invest. 2007, 117 (10), pp 2903-2912), d) in excitotoxic DNA fragmentation via mitochondrial pathways (J Takano et al., J Biol Chem. 2005, 280 (16) pp. 16175-16184), and in e) necrotic processes in dystrophic muscles (M J Spencer et al., Hum Mol Gen, 2002, 11(21), pp 2645-2655).

It is also known that calpains are linked to Alzheimer disease (AD) (Nixon R. A., "The calpains in aging and aging-related diseases", Ageing Res Rev. 2003 October; 2(4):407-18). Calpain 1 is abnormally activated in AD brain (Saito K, et al. "Widespread activation of calcium-activated neutral proteinase (calpain) in the brain in Alzheimer disease: a potential molecular basis for neuronal degeneration", Proc Natl Acad Sci USA. 1993 Apr. 1; 90(7):2628-32). Calpastatin, the endogenous inhibitor of calpains, is significantly decreased in the same neurodegenerative disorder (Nixon R. A., "The calpains in aging and aging-related diseases", Ageing Res Rev. 2003 October; 2(4):407-18). Calpain overactivation triggered by abnormally high calcium levels and calpastatin depletion lead to limited cleavage or degradation of key neuronal proteins in AD (Wang K K, "Calpain and caspase: can you tell the difference?", Trends Neurosci. 2000 January; 23(1):20-6). Calpains indirectly modulate the proteolytic processing of the amyloid precursor protein (APP), a polypeptide thought to play a fundamental role in AD (Siman R. at al. "Proteolytic processing of beta-amyloid precursor by calpain I", J Neurosci. 1990 July; 10(7):2400-11).

Other calpain substrates affected in AD include CaM-kinase IIα (CaMK-IIα) and PKC, 2 enzymes that regulate APP phosphorylation and influence its metabolism (Wang K K et al., "Development and therapeutic potential of calpain inhibitors" Adv Pharmacol. 1997; 37( ):117-52); second messenger-related enzymes such as phospholipase C-1, -2, -β3 (Banno Y. et al, "Endogenous cleavage of phospholipase C-beta 3 by agonist-induced activation of calpain in human platelets", J Biol Chem. 1995 Mar. 3; 270(9):4318-24), and cyclin-dependent kinase 5 (Cdk-5) (Lee M S. et al, "Neurotoxicity induces cleavage of p35 to p25 by calpain", Nature. 2000 May 18; 405(6784):360-4); transcription factors such as c-Jun, c-Fos, and IκB (Carillo S, "Differential sensitivity of FOS and JUN family members to calpains", Oncogene. 1994 June; 9(6):1679-89 and Lin Y C, "Activation of NF-kappa B requires proteolysis of the inhibitor I kappa B-alpha: signal-induced phosphorylation of I kappa B-alpha alone does not release active NF-kappa B", Proc Natl Acad Sci USA. 1995 Jan. 17; 92(2):552-6); and the memory-related gene, cAMP regulatory element-binding protein (CREB) (Mbebi C, "Amyloid precursor protein family-induced neuronal death is mediated by impairment of the neuroprotective calcium/calmodulin protein kinase IV-dependent signalling pathway", J Biol Chem. 2002 Jun. 7; 277(23):20979-90). Recently, calpain actions on the GluR1 subunit of AMPA receptors (24), amphiphysin I (25) and suprachiasmatic nucleus circadian oscillatory protein (26), have been shown to modulate synaptic activity and memory formation.

Growing evidence suggests that the cognitive impairment in AD starts long before neuronal death and that signalling between neurons is interrupted at early stages of the disease. The importance of synaptic alterations in AD has been confirmed by studies on transgenic mouse models of AD (Sant'Angelo A, "Usefulness of behavioral and electrophysiological studies in transgenic models of Alzheimer's disease", Neurochem Res. 2003 July; 28(7):1009-15) and on amyloid-β peptide-induced (Aβ-induced) impairment of long-term potentiation (LTP), a widely studied cellular model of learning and memory (Bliss T V. et al, "A synaptic model of memory: long-term potentiation in the hippocampus"; Collingridge G L Nature. 1993 Jan. 7; 361(6407):31-9).

Moreover, calpains influence the phosphorylation and proteolysis of tau, another protein associated with AD (Wang K K, "Calpain and caspase: can you tell the difference?", Trends Neurosci. 2000 January; 23(1):20-6). Accumulation of phosphorylated tau additionally leads to the formation of so-called neurofibrillary tangles (NFTs) which, together with the well-known amyloid plaques, represent a pathological hallmark of Alzheimer's disease. Similar changes in the tau protein, generally referred to important feature of as tauopathies are also observed in other (neuro) degenerative disorders such as, for example, following stroke, inflammations of the brain, Parkinsonism, in normal pressure hydrocephalus and Creutzfeldt-Jakob disease.

The involvement of calpain in neurodegenerative processes has been demonstrated in transgenic mice with the aid of calpastatin, a specific and natural inhibitor of calpains (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the A@-induced degeneration of neurons (Park et al.; J. Neurosci. 2005, 25, pp. 5365-5375), and in addition reduce the release of the (3-amyloid precursor protein(β APP) (J. Higaki et al., Neuron, 1995, I4, pp. 651-659).

With this background, calpain inhibitors represent a novel therapeutic principle for the treatment of neurodegenerative disorders in general and in particular Alzheimer's disease, Parkinson disease, multiple sclerosis, acute autoimmune encephalitis, and Creutzfeldt-Jakob disease.

It has been demonstrated that the HIV-induced neurotoxicity is mediated by calpain (O'Donnell et al.; J. Neurosci. 2006, 26 (3), pp. 981-990) and the involvement of calpain in the replication of the HIV virus has also been shown (Teranishi et al.; Biochem. Biophys. Res. Comm. 2003, 303 (3), pp. 940-946).

The involvement of calpain in the development of kidney diseases, such as chronic kidney diseases, e.g. diabetic nephropathy, has also been recently demonstrated. Thus, it has been demonstrated by Y. Shi et al. in animal models that the natural calpain inhibitor calpastatin is down regulated during renal ischemia reperfusion (Am. J. Physiol. Renal Physiol. 2000, 279, pp. 509-517). Furthermore, A Dnyanmote et al., Toxicology and Applied Pharmacology 2006, 215, pp. 146-157, have shown that inhibition of calpain via overexpression of calpastatin reduces the progression of DCVC-induced renal injury in a model of acute renal failure. In addition, Peltier et al. have demonstrated that calpain activation and secretion promotes glomerular injury in experimental glomerulonephritis (J. Am. Soc. Nephrol. 2006, 17, pp. 3415-3423). It has also been shown that calpain inhibitors reduce renal dysfunction and injury caused by renal ischemia-reperfusion and thus may be useful in enhancing the tolerance of the kidney against renal injury associated with aortovascular surgery or renal transplantation (P. Chatterjee et al., Biochem. Pharmacal. 2005, 7, pp. 1121-1131). On this basis calpain inhibition may be considered a therapy principle useful in the treatment of kidney diseases, such as chronic kidney diseases, e.g. diabetic nephropathy.

Calpain has also been identified as a central mediator essential for parasitic activity. Parasites like *Plasmodium falciparum* and *Toxoplasma gondii* exploit host cell calpains to facilitate escape from the intracellular parasitophorous vacuole and/or host plasma membrane. Inhibition of calpain-1 in hypotonically lysed and resealed erythrocytes prevented the escape of *P. falciparum* parasites, which was restored by adding purified calpain-1. Similarly, efficient egress of *T. gondii* from mammalian fibroblasts was blocked by either small interfering RNA-mediated suppression or genetic deletion of calpain activity and could be restored by genetic complementation (D. Greenbaum et al., Science 324, 794 (2009)). Because parasites that fail to escape from their host cells are unable to proliferate, suggesting a strategy for anti-parasitic therapeutics. Pharmacological inhibition of calpain has been shown to exert anti-malarial activity, and hence presents a novel strategy for anti-parasitic strategy such as diseases caused by protest infections like malaria or toxoplasmosis (Li et al., Mol Biochem Parasitol. 2007; 155(1): 26-32; Jung et al. Archives of Pharmacal Research (2009), 32(6), 899-906, Chandramohanadas et al. Science (2009), 324, 794).

It has also been reported (Leloup and Wells, Expert Opin Ther Targets., 2011, 15(3), 309-323; Storr et al., Nat Rev Cancer., 2011, 11(5), 364-374; Storr et al., Pathobiology, 2015, 82(3-4), 133-141; Selvakumar and Sharma, Experimental Therapeutic Medicine, 2010, 1, 413-417; Storr et al., Oncotarget, 2016, 30(7), 47927-47937; and Guan et al., Proc Amer Assoc Cancer Res., 2005, 46) that calpains, in particular calpain 1 and calpain 2, are involved in a wide variety of common cancers such as breast cancer, colorectal cancer and leukaemia. Calpains 1 and 2 are involved in the development and progression of cancer by allowing cell transformation, the migration and the invasion of tumour cells, and the neovascularization of the tumour. These reports also mention that numerous tumour cells present an abnormally high activity of these calpains. Thus, inhibiting calpain activity would be an efficient way to block the development of a tumour by blocking the transformation and the proliferation of the cells, as well as the vascularization of the tumour.

Fibrosis refers to the accumulation of extracellular matrix molecules that make up scar tissue (collagen-rich extracellular matrix) and is the common feature of fibrotic diseases. Fibrotic diseases can affect any organ, such as kidney, liver, lungs, skin, heart and eye, leading to organ dysfunction and failure and potentially death. In epithelial organs, especially the lung, liver skin and kidney, the replacement of normal functional units of cells with collagen-rich scar tissue and the architectural distortion cause by scar retraction are the major factors in progressive loss of organ function and eventual failure [Friedman et al. Science Translational Medicine, 2013, 5, 167]. Calpain activity has been described as essential in wound healing and scar formation [Nassar et al., PLoS ONE, 2012, 7(5), e37084]. Calpains have also been reported as being involved in fibrotic diseases [WO 2017/156074 A1; Buckman et al., Am J Respir Crit Care Med, 2018, 197, A5747; Potz et al., J Nat Sci 2016, 2(9), e218; Ono et al., Nature Reviews Drug Discovery, 2016, 15, 854-876], such as liver fibrosis (alcoholic, viral, autoimmune, metabolic and hereditary chronic disease), renal fibrosis (e.g. resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, among others), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia and other blood disorders), cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, especially surgical implants, injection fibrosis and secondary conditions and disease states of fibrosis, such as cirrhosis, diffuse parenchymal lung disease, post-vasectomy pain syndrome and arthrofibrosis, among others. A particular calpain inhibitor, BLD-2660, is currently undergoing phase 1 clinical trials for fibrosis. Thus, inhibiting calpain activity would be an effective strategy for managing fibrotic diseases.

WO 2004/078908 A2 and WO 2005/056519 A1 disclose calpain inhibitors with potential to inhibit calpain 1 in the treatment of different diseases including Alzheimer's disease. In particular, example 17 of WO 2005/056519 A1, which has been assigned the code name SNJ-1945, has proved to be effective in reducing the experimental autoimmune encephalomyelitis (EAE) clinical scores in vivo (Trager N. et al., "Effects of a novel orally administered calpain inhibitor SNJ-1945 on immunomodulation and neurodegeneration in a murine model of multiples sclerosis", J. Neurochem. 2014 July; 130(2): 268-279).

There remains a need for new strategies for the management of diseases or conditions associated with elevated calpain activity, such as heart injury caused by infarction, ischemia with or without reperfusion; neurodegenerative disorders; malaria; diabetic nephropathy; neurotoxicity induced by HIV virus; cancer; and fibrotic diseases.

SUMMARY OF THE INVENTION

The authors of the present invention have surprisingly found that compounds of formula (I), which have a methoxy group in the meta position of the phenyl ring, are potent calpain-1 inhibitors. The position of this group is of outmost importance for achieving high potency in calpain-1 inhibition, as shown in the comparative examples. Thus, these compounds of formula (I) are useful for the treatment and/or prevention of diseases or conditions associated with an elevated calpain activity, such as heart injury caused by infarction, ischemia with or without reperfusion; neurodegenerative disorders; malaria; diabetic nephropathy; neurotoxicity induced by HIV virus; and cancer.

In a first aspect, the present invention relates to a compound of formula (I):

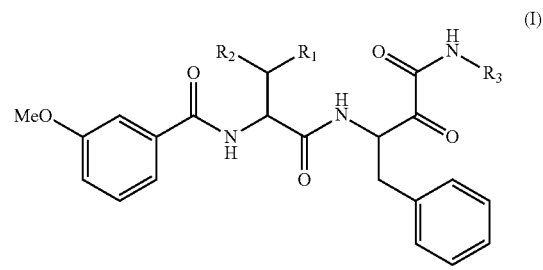

wherein
$R_1$ is selected from the group consisting of $C_1$-$C_6$ alkyl and $C_3$-$C_6$ cycloalkyl,
$R_2$ is selected from the group consisting of H and $C_1$-$C_6$ alkyl,
$R_3$ is selected from the group consisting of $C_1$-$C_6$ alkoxy and $C_3$-$C_6$ cycloalkyl,
or a pharmaceutically acceptable salt or stereoisomer thereof, for use in the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In a second aspect, the present invention relates to a pharmaceutical composition comprising a compound of formula (I) as defined in the first aspect and a pharmaceutically acceptable excipient for use in the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In another aspect, the present invention relates to the use of a compound of formula (I) as defined in the first aspect or a pharmaceutical composition comprising said compound and a pharmaceutically acceptable excipient, for the manufacture of a medicament for the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In another aspect, the present invention relates to a method of treatment and/or prevention a disease or condition selected from the group consisting of heart injury caused by infarction, ischemia with or without reperfusion; neurodegenerative disorders; malaria; diabetic nephropathy; neurotoxicity induced by HIV virus; cancer, and fibrotic diseases, the method comprising administering to a subject in need thereof a therapeutically effective amount of a compound of formula (I) as defined in the first aspect or a pharmaceutical composition comprising said compound and a pharmaceutically acceptable excipient.

In a further aspect, the present invention relates to a compound of formula (II):

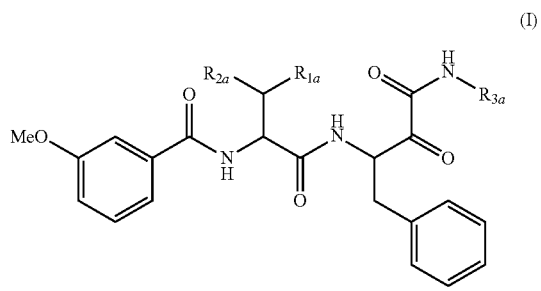

(I)

wherein $R_{1a}$ is selected from the group consisting of $C_1$-$C_6$ alkyl and $C_3$-$C_6$ cycloalkyl, $R_{2a}$ is selected from the group consisting of H and $C_1$-$C_6$ alkyl, $R_{3a}$ is $C_3$-$C_6$ cycloalkyl, or a pharmaceutically acceptable salt or stereoisomer thereof.

In another aspect, the present invention relates to a pharmaceutical composition comprising a compound of formula (II) as defined in the third aspect and a pharmaceutically acceptable excipient.

In another aspect, the present invention relates to a compound of formula (II) as defined in the third aspect or pharmaceutical composition as defined in the fourth aspect for use in medicine, in particular for the treatment and/or prevention of a disease or condition associated with an elevated calpain activity; preferably selected from the group consisting of heart injury caused by infarction, ischemia with or without reperfusion; neurodegenerative disorders; malaria; diabetic nephropathy; neurotoxicity induced by HIV virus; cancer; and fibrotic diseases.

DETAILED DESCRIPTION OF THE INVENTION

Definitions

Some definitions are included with the aim of facilitating the understanding of the invention.

The term "alkyl" as employed herein alone or as part of another group designates a linear or branched saturated monovalent hydrocarbon chain containing the number of carbon atoms indicated in each case which is typically from of one to six carbon atoms, and preferably from one to three. Examples of alkyls are methyl, ethyl, propyl, 2-propyl, n-butyl, isobutyl, sec-butyl, tert-butyl, n-pentyl, isopentyl, sec-pentyl, tert-pentyl, neopentyl, and the like.

The term "alkoxy" as employed herein alone or as a part of another group designates an alkyl group as defined above linked through oxygen, i.e. alkyl-O—. Examples of alkoxy include methoxy, ethoxy, isopropoxy, tertbutoxy, and the like.

The term "cycloalkyl" as employed herein alone or as a part of another group designates a monocyclic radical which is saturated or partially saturated, preferably saturated, and which consist solely of carbon and hydrogen atoms and containing the number of carbon atoms indicated in each case which his typically from 3 to 6 and preferably from 3 to 5. Examples of cycloalkyls are cyclopropyl, cyclobutyl, cyclopentyl, cyclohexyl.

The term "salt" must be understood as any form of a compound according to the present invention, in which said compound is in ionic form or is charged and coupled to a counter-ion (a cation or anion) or is in solution. This definition also includes quaternary ammonium salts. The definition includes in particular pharmaceutically acceptable salts. The term "pharmaceutically acceptable salt" embraces salts with a pharmaceutically acceptable acid or base, which are synthesized from the parent compound which contains an acidic moiety by addition of a pharmaceutically acceptable base, or which are synthesized from the parent compound which contains a basic moiety by addition of a pharmaceutically acceptable acid. Pharmaceutically acceptable acids include both inorganic acids, for example, hydrochloric, sulfuric, phosphoric, diphosphoric, hydrobromic, hydroiodic, and nitric acid, and organic acids, for example, citric, fumaric, maleic, malic, mandelic, ascorbic, oxalic, succinic, tartaric, benzoic, acetic, methanesulfonic (mesylate), ethanesulfonic, benzenesulfonic (besylate), or p-toluenesulfonic (tosylate) acid. Pharmaceutically acceptable bases include alkali metal (e.g., sodium or potassium) and alkali earth metal (e.g., calcium or magnesium) hydroxides and organic bases, such as alkyl amines, arylalkyl amines, and heterocyclic amines. For instance, pharmaceutically acceptable salts of compounds provided herein are synthesized from the parent compound which contains a basic or an acid moiety by conventional chemical methods. Generally, such salts are, for example, prepared by reacting the free base or free acid forms of these compounds with a stoichiometric amount of the appropriate acid or base, respectively, in water or in an organic solvent or in a mixture of the two.

All stereoisomers of the compounds of this invention are contemplated either alone or as mixtures thereof. The process of preparation can utilize racemates, enantiomers, or diastereomers as starting materials. When diastereomeric or enantiomeric products are prepared, they can be separated by conventional methods, for example, chromatographic or functional crystallization.

Unless otherwise stated, the compounds of the invention are also meant to include compounds which differ only in the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon or $^{15}$N-enriched nitrogen are within the scope of this invention.

Certain compounds of the present invention can exist in unsolvated forms as well as solvated forms, including hydrated forms. In general, the solvated forms are equivalent to unsolvated forms and are encompassed within the scope of the present invention.

Certain compounds of the present invention may exist in multiple crystalline or amorphous forms. In general, all physical forms are equivalent for the uses contemplated by the present invention and are intended to be within the scope of the present invention.

The term "prevention", as used herein, refers to the administration of a compound of the invention in an initial or early stage of a disease or condition, or to also prevent its onset.

The term "treatment" is used to designate the administration of a compound of the invention to control disorder progression before or after the clinical signs had appeared. By control of the disorder progression it is meant to designate beneficial or desired clinical results including, but not limited to, reduction of symptoms, reduction of the length of the disorder, stabilization pathological state (specifically avoidance of further deterioration), delay in the disorder's progression, improvement of the pathological state and remission (both partial and total).

The term "subject", as used herein, refers to any animal or human that is suffering from one of the diseases or conditions disclosed herein. Preferably, the subject is a mammal. The term "mammal", as used herein, refers to any mammalian species, including but not being limited to domestic and farm animals (cows, horses, pigs, sheep, goats, dogs, cats or rodents), primates, and humans. Preferably, the mammal is a human being.

The term "heart injury", as used herein, refers to any damage in cardiac tissue caused by infarction, ischemia with or without reperfusion, such as remodeling.

The term "remodeling", as used herein, refers to a group of molecular, cellular and interstitial changes that clinically manifest as changes in size, shape and function of the heart resulting from cardiac injury, such as changes in the cavity diameter, mass (hypertrophy and atrophy), geometry (heart wall thickness and shape), areas of scar, fibrosis and inflammatory infiltrate. Cardiac dysfunction is the main consequence of cardiac remodeling, which consists of a pathophysiological substrate for the onset and progression of ventricular dysfunction. This interaction starts with genetic changes in response to a cardiac injury, with reexpression of fetal genes. Consequently, cellular and molecular changes occur, resulting in progressive loss of ventricular function, asymptomatic at first that evolves to signs and symptoms of heart failure. Cardiac remodeling is associated with malignant ventricular arrhythmias, including sustained ventricular tachycardia and ventricular fibrillation. During the first hours after coronary occlusion, disintegration of interfibrillar collagen may occur simultaneously with necrosis of myofibrils. The loss of sustaining tissue makes this area more susceptible to distension and deformation. Thinning of the infarcted region and dilation of the cavity occur as a consequence of slippage of necrotic muscle cells and rearrangement of the myocytes across the infarcted wall. This acute ventricular dilation, characterized by thinning and lengthening of the infarct is termed infarct expansion. Infarct expansion increases the likelihood of myocardial rupture and represents an anatomical substrate for aneurysms.

The term "neurodegenerative disorders", as used herein, refers to disorders which result in progressive degeneration and/or death of neuron cells. Examples of neurodegenerative disorders are Alzheimer's disease, Parkinson disease, multiple sclerosis, acute autoimmune encephalitis and Creutzfeldt-Jakob disease.

The term "cancer" or "tumour", as used herein, refers to a broad group of diseases involving unregulated cell growth and which are also referred to as malignant neoplasms. The term is usually applied to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. Biological processes known to be related to cancer include angiogenesis, immune cell infiltration, cell migration and metastasis. Cancers usually share some of the following characteristics: sustaining proliferative signalling, evading growth suppressors, resisting cell death, enabling replicative immortality, inducing angiogenesis, and activating invasion and eventually metastasis. Cancers invade nearby parts of the body and may also spread to more distant parts of the body through the lymphatic system or bloodstream. Cancers are classified by the type of cell that the tumour cells resemble, which is therefore presumed to be the origin of the tumour.

Cancers that can be treated or prevented by the medical uses of the present invention are solid tumours, e.g. colorectal cancer, breast cancer, lung cancer, pancreatic cancer, larynx cancer, tongue cancer, ovarian cancer, prostate cancer, liver cancer, head and neck cancer, oesophageal cancer, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, dysgerminoma, embryonal carcinoma, Wilms' tumour, cervical cancer, testicular tumour, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, and leukaemia; preferably breast cancer, colorectal cancer and leukaemia.

The term "leukaemia", as used herein, refers to a type of cancer of the blood or bone marrow characterized by an abnormal increase of immature white blood cells called blasts and that originates in blood-forming tissue. Leukaemia starts in the bone marrow where developing blood cells, usually developing white cells, undergo a malignant (cancerous) change. This means that they multiply in an uncontrolled way crowding the marrow and interfering with normal blood cell production. Increasing numbers of abnormal cells, called blast cells or leukemic blasts eventually spill out of the bone marrow and travel around the body in the blood stream. In some cases these abnormal cells accumulate in various organs including the lymph nodes, spleen, liver and central nervous system (brain and spinal cord). There are four major kinds of leukaemia: Acute lymphoblastic leukaemia, or ALL; Acute myeloid leukaemia, or AML; Chronic lymphocytic leukaemia, or CLL; Chronic myelogenous leukaemia, or CML.

The term "fibrotic disease", as used herein, refers to a group of diseases which involve the formation of excess fibrous connective tissue in an organ or tissue. Fibrosis results in scaring and thickening of the affected tissue. Fibrosis can occur in many tissues of the body, resulting in a variety of fibrotic diseases, such as cardiac fibrosis, lung fibrosis, liver fibrosis, renal fibrosis, retroperitoneal fibrosis, hypersensitivity pneumonitis, interstitial fibrosis, systemic scleroderma, macular degeneration, pancreatic fibrosis, fibrosis of the spleen, mediastinal fibrosis, myelofibrosis, endomyocardial fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome and arthrofibrosis. Preferably the fibrotic disease refers to cardiac fibrosis, lung fibrosis, liver fibrosis, renal fibrosis or retroperitoneal fibrosis.

Compounds of Formula (I)

In the first aspect, the present invention provides a compound of formula (I)

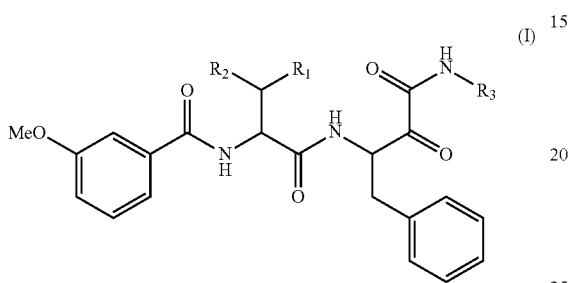

(I)

wherein
$R_1$ is selected from the group consisting of $C_1$-$C_6$ alkyl and $C_3$-$C_6$ cycloalkyl,
$R_2$ is selected from the group consisting of H and $C_1$-$C_6$ alkyl,
$R_3$ is selected from the group consisting of $C_1$-$C_6$ alkoxy and $C_3$-$C_6$ cycloalkyl,
or a pharmaceutically acceptable salt or stereoisomer thereof, for use in the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In a particular embodiment, $R_1$ is selected from the group consisting of $C_1$-$C_3$ alkyl and $C_3$-$C_5$ cycloalkyl; preferably from the group consisting of methyl, ethyl, propyl, isopropyl, cyclopropyl, cyclobutyl and cyclopentyl; more preferably from the group consisting of methyl, isopropyl and cyclopropyl; still more preferably from the group consisting of isopropyl and cyclopropyl; the most preferred is cyclopropyl.

In another particular embodiment, $R_2$ is selected from the group consisting of H and $C_1$-$C_3$ alkyl; preferably from the group consisting of H, methyl, ethyl, propyl and isopropyl; more preferably from the group consisting of H and methyl; the most preferred is H.

In another particular embodiment, $R_3$ is selected from the group consisting of $C_1$-$C_3$ alkoxy and $C_3$-$C_5$ cycloalkyl; preferably from the group consisting of methoxy, ethoxy, propoxy, isopropoxy, cyclopropyl, cyclobutyl and cyclopentyl; still more preferably from the group consisting of methoxy and cyclopropyl; the most preferred is cyclopropyl. In another particular embodiment, $R_3$ is $C_3$-$C_6$ cycloalkyl; preferably $C_3$-$C_5$ cycloalkyl; preferably cyclopropyl, cyclobutyl or cyclopentyl; the most preferred is cyclopropyl.

In a particular embodiment, $R_1$ is selected from the group consisting of $C_1$-$C_3$ alkyl and $C_3$-$C_5$ cycloalkyl; $R_2$ is selected from the group consisting of H and $C_1$-$C_3$ alkyl; and $R_3$ is selected from the group consisting of $C_1$-$C_3$ alkoxy and $C_3$-$C_5$ cycloalkyl.

In another particular embodiment, $R_1$ is selected from the group consisting of $C_1$-$C_3$ alkyl and $C_3$-$C_5$ cycloalkyl; $R_2$ is selected from the group consisting of H and $C_1$-$C_3$ alkyl; and $R_3$ is $C_3$-$C_5$ cycloalkyl.

In another particular embodiment, $R_1$ is selected from the group consisting of isopropyl and cyclopropyl; $R_2$ is H; and $R_3$ is cyclopropyl.

In a particular embodiment, the compound of formula (I) is a compound of formula (Ia):

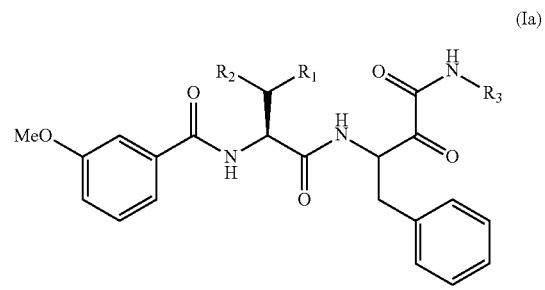

(Ia)

wherein $R_1$, $R_2$ and $R_3$ have the same meaning as in the compounds of formula (I), or a stereoisomer or a pharmaceutically acceptable salt thereof.

In a particular embodiment, the specific stereoisomer of the compound of formula (I) is a compound of formula (Ib):

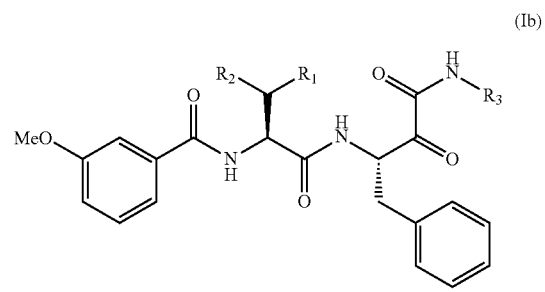

(Ib)

wherein $R_1$, $R_2$ and $R_3$ have the same meaning as in the compounds of formula (I), or a pharmaceutically acceptable salt thereof.

In a preferred embodiment, the compound of formula (I) is selected from the group consisting of:

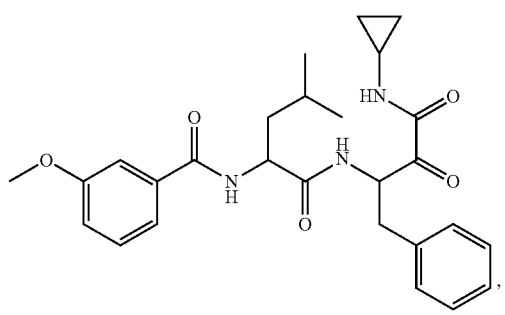

-continued
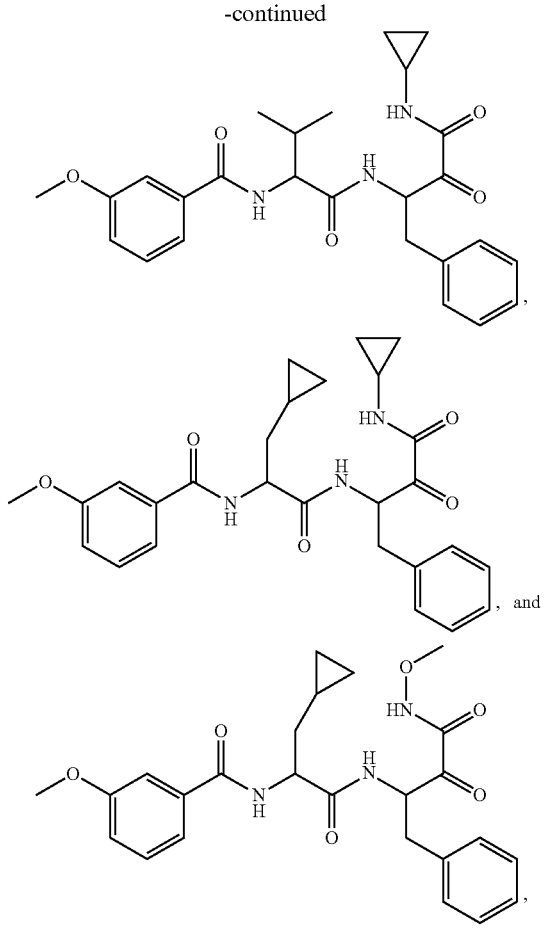
, and
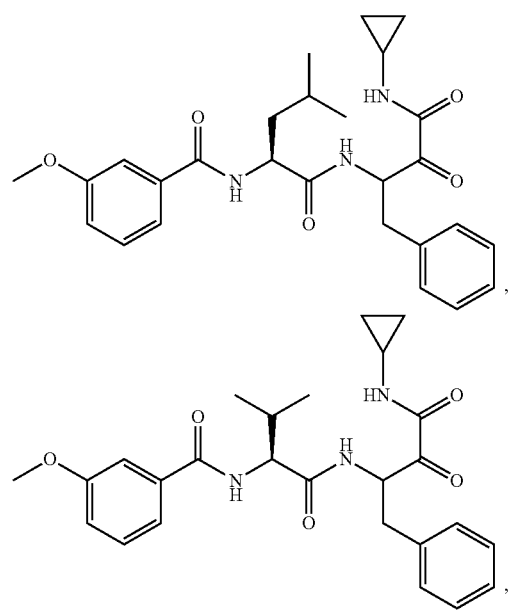
,
or a stereoisomer or pharmaceutically acceptable salt thereof.
In a particular embodiment, the compound of formula (Ia) is selected from the group consisting of:
-continued
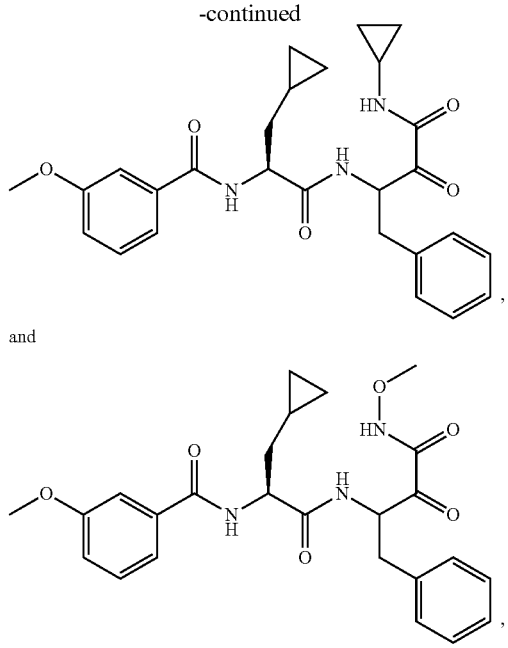
and
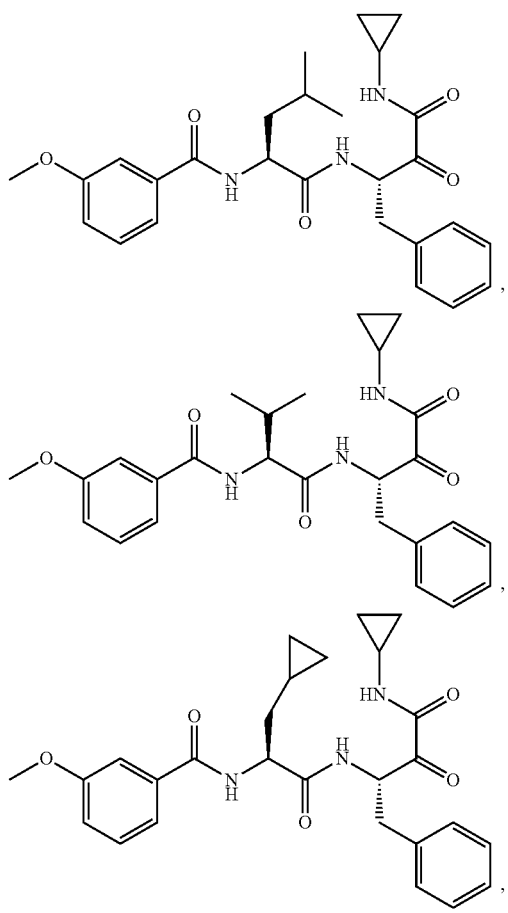
,
or a stereoisomer or pharmaceutically acceptable salt thereof.
In a particular embodiment, the compound of formula (Ib) is selected from the group consisting of:

and

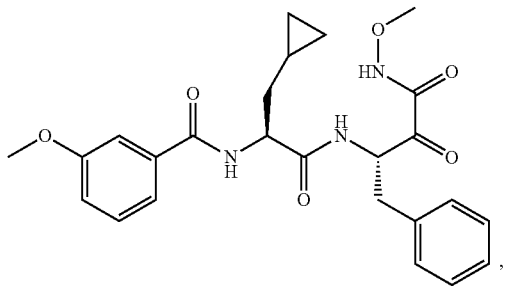

, or a pharmaceutically acceptable salt thereof.

In a particular embodiment, the compound of formula (I) is for use in the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; and cancer.

In a preferred embodiment, the compound of formula (I) is for use in the treatment and/or prevention of heart injury caused by infarction, ischemia with or without reperfusion, preferably remodeling after myocardial infarction.

In a particular embodiment, the compound of formula (I) is for use in the treatment and/or prevention of a neurodegenerative disorder selected from the group consisting of Alzheimer's disease, Parkinson disease, multiple sclerosis, acute autoimmune encephalitis, and Creutzfeldt-Jakob disease.

In another particular embodiment, the compound of formula (I) is for use in the treatment and/or prevention of a cancer selected from the group consisting of breast cancer, colorectal cancer and leukaemia.

In another particular embodiment, the compound of formula (I) is for use in the treatment and/or prevention of a fibrotic disease selected from the group consisting of cardiac fibrosis, lung fibrosis, liver fibrosis, renal fibrosis and retroperitoneal fibrosis.

In a second aspect, the present invention relates to a pharmaceutical composition comprising a compound of formula (I) as defined in the first aspect and a pharmaceutically acceptable excipient for use in the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In another aspect, the invention relates to the use of a compound of formula (I) as defined above, or pharmaceutically acceptable salt or stereoisomer thereof, for the manufacture of a medicament for the treatment and/or prevention of a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases.

In a further aspect, the present invention relates to a method of treatment and/or prevention a disease or condition selected from the group consisting of heart injury caused by infarction, ischemia with or without reperfusion; neurodegenerative disorders; malaria; diabetic nephropathy; neurotoxicity induced by HIV virus; cancer; and fibrotic diseases, which comprises administering to a subject in need thereof a therapeutically effective amount of a compound of formula (I) as defined above or a pharmaceutically acceptable salt or stereoisomer thereof.

In particular embodiments of the uses and methods of treatment defined above, the disease or condition is selected from the group consisting of heart injury caused by infarction, ischemia with or without reperfusion; neurodegenerative disorders; malaria; diabetic nephropathy; neurotoxicity induced by HIV virus; and cancer.

In other particular embodiments of the uses and methods of treatment defined above a preferred embodiment, the disease or condition is heart injury caused by infarction, ischemia with or without reperfusion, preferably remodeling after myocardial infarction.

In other particular embodiments of the uses and methods of treatment defined above the neurodegenerative disorder is selected from the group consisting of Alzheimer's disease, Parkinson disease, multiple sclerosis, acute autoimmune encephalitis, and Creutzfeldt-Jakob disease.

In other particular embodiments of the uses and methods of treatment defined above the cancer is selected from the group consisting of breast cancer, colorectal cancer and leukaemia.

In other particular embodiments of the uses and methods of treatment defined above the fibrotic disease is selected from the group consisting of cardiac fibrosis, lung fibrosis, liver fibrosis, renal fibrosis and retroperitoneal fibrosis.

Compounds of Formula (II)

In the third aspect, the present invention provides a compound of formula (II):

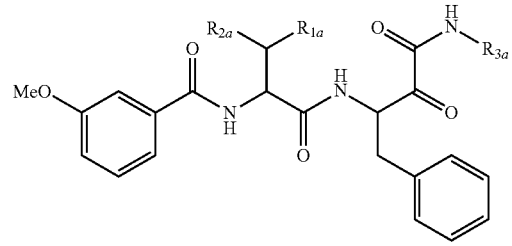

(II)

wherein $R_{1a}$ is selected from the group consisting of $C_1$-$C_6$ alkyl and $C_3$-$C_6$ cycloalkyl, $R_{2a}$ is selected from the group consisting of H and $C_1$-$C_6$ alkyl, $R_{3a}$ is $C_3$-$C_6$ cycloalkyl, or a pharmaceutically acceptable salt or stereoisomer thereof.

Compounds of formula (II) are a subgroup of compounds of formula (I).

In a particular embodiment, $R_{1a}$ is selected from the group consisting of $C_1$-$C_3$ alkyl and $C_3$-$C_5$ cycloalkyl; preferably from the group consisting of methyl, ethyl, propyl, isopropyl, cyclopropyl, cyclobutyl and cyclopentyl; more preferably from the group consisting of methyl, isopropyl and cyclopropyl; still more preferably from the group consisting of isopropyl and cyclopropyl; the most preferred is cyclopropyl.

In another particular embodiment, $R_{2a}$ is selected from the group consisting of H and $C_1$-$C_3$ alkyl; preferably from the group consisting of H, methyl, ethyl, propyl and isopropyl; more preferably from the group consisting of H and methyl; the most preferred is H.

In another particular embodiment, $R_{3a}$ is $C_3$-$C_6$ cycloalkyl; preferably $C_3$-$C_5$ cycloalkyl; preferably cyclopropyl, cyclobutyl or cyclopentyl; the most preferred is cyclopropyl.

In a particular embodiment, $R_{1a}$ is selected from the group consisting of $C_1$-$C_3$ alkyl and $C_3$-$C_5$ cycloalkyl; $R_{2a}$ is selected from the group consisting of H and $C_1$-$C_3$ alkyl; and $R_{3a}$ is $C_3$-$C_5$ cycloalkyl.

In another particular embodiment, $R_{1a}$ is selected from the group consisting of isopropyl and cyclopropyl; $R_{2a}$ is H; and $R_{3a}$ is cyclopropyl.

In a particular embodiment, the compound of formula (II) is a compound of formula (IIa):

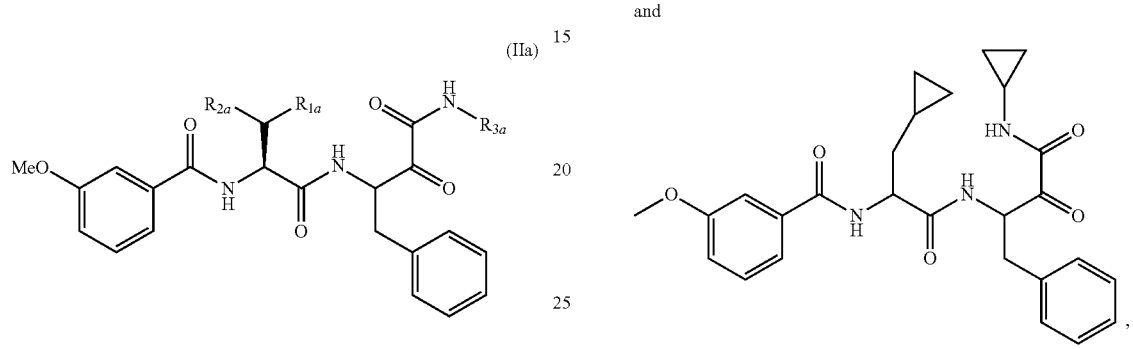

(IIa)

wherein $R_{1a}$, $R_{2a}$ and $R_{3a}$ have the same meaning as in the compounds of formula (II), or a stereoisomer or a pharmaceutically acceptable salt thereof.

In a particular embodiment, the specific stereoisomer of the compound of formula (II) is a compound of formula (IIb):

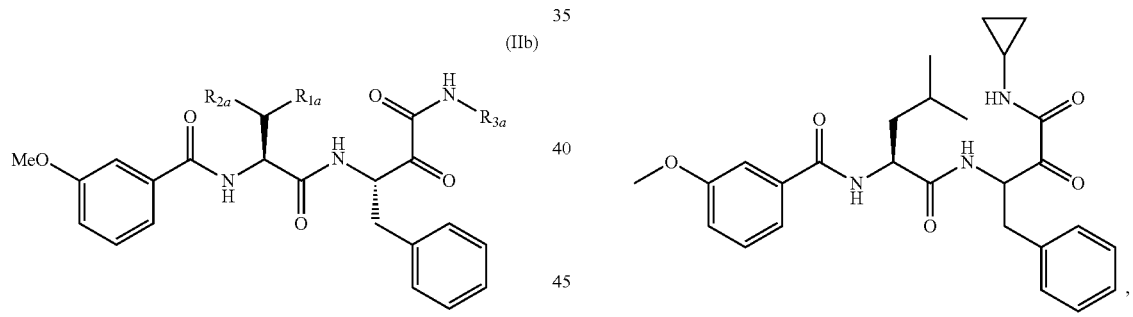

(IIb)

wherein $R_{1a}$, $R_{2a}$ and $R_{3a}$ have the same meanings as defined for the compounds of formula (II), or a pharmaceutically acceptable salt thereof.

In a preferred embodiment, the compound of formula (II) is selected from the group consisting of:

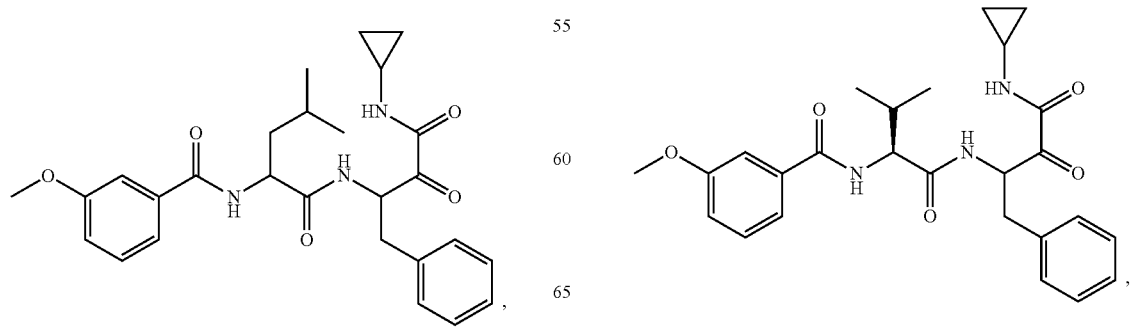

,

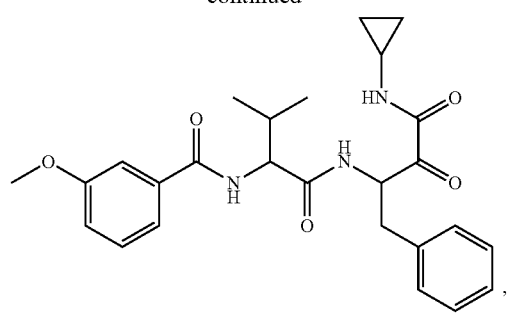

, and

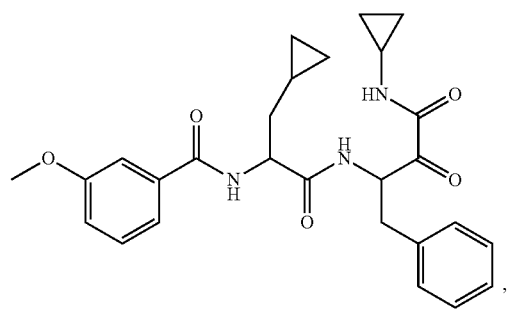

, or a stereoisomer or pharmaceutically acceptable salt thereof.

In a particular embodiment, the compound of formula (IIa) is selected from the group consisting of:

and

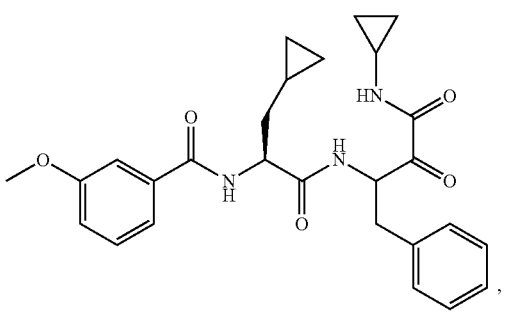

or a stereoisomer or pharmaceutically acceptable salt thereof.

In a particular embodiment, the compound of formula (IIb) is selected from the group consisting of

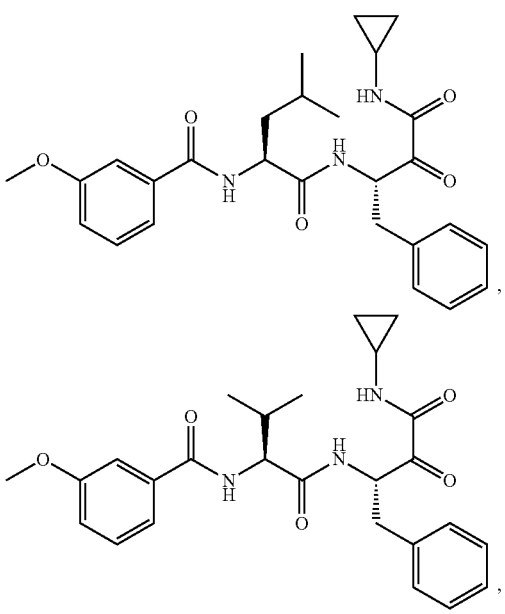

and

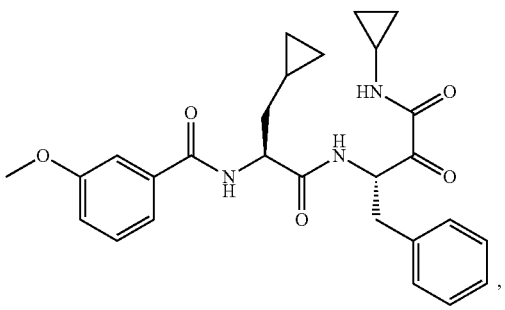

or a pharmaceutically acceptable salt thereof.

Pharmaceutical Compositions

In another aspect, the present invention provides a pharmaceutical composition comprising a compound of formula (II) as defined above, or a stereoisomer or pharmaceutically acceptable salt thereof, and one or more pharmaceutically acceptable excipients.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

Compounds of formula (II) of the invention may be administered by the oral, sublingual, parenteral, subcutaneous, intramuscular, intravenous, transdermal, intranasal, intraocular, and/or rectal routes. The compounds may be administered alone or in combination with one or more other compounds of the invention or one or more other drugs.

The pharmaceutical compositions of the present invention may comprise the compounds of formula (II) within liposomes or microvesicles, and may be in the form of dispersions, solutions, lotions, gels, and the like, including topical preparations.

The above definitions do also apply to pharmaceutical compositions comprising a compound of formula (I).

Use of Compounds of Formula (II)

As explained above, the compounds of formula (II) are a subgroup of the compounds of formula (I). Thus, the compounds of formula (II) are also inhibitors of calpain-1. Accordingly, in a fourth aspect, the present invention relates to compounds of formula (II) for use in medicine, in particular for the treatment and/or prevention of diseases or conditions associated with an elevated calpain activity. Preferred diseases or conditions are those selected from the group consisting of heart injury caused by infarction, ischemia with or without reperfusion; neurodegenerative disorders; malaria; diabetic nephropathy; neurotoxicity induced by HIV virus; and cancer such as heart injury caused by infarction, ischemia with or without reperfusion; neurodegenerative disorders; malaria; diabetic nephropathy; neurotoxicity induced by HIV virus; cancer; and fibrotic diseases; a more preferred disease or condition is heart injury caused by infarction, ischemia with or without reperfusion, preferably remodeling after myocardial infarction.

In another aspect, the invention relates to the use of a compound of formula (II) as defined above, or pharmaceutically acceptable salt or stereoisomer thereof, for the manufacture of a medicament for the treatment and/or prevention of a disease or condition associated with an elevated calpain activity; preferably selected from the group consisting of heart injury caused by infarction, ischemia with or without reperfusion; neurodegenerative disorders; malaria; diabetic nephropathy; neurotoxicity induced by HIV virus; cancer; and fibrotic diseases; more preferably selected from the group consisting of heart injury caused by infarction, ischemia with or without reperfusion, still more preferably remodeling after myocardial infarction.

In a further aspect, the present invention relates to a method of treatment and/or prevention a disease or condition associated with an elevated calpain activity which comprises administering to a subject in need thereof a therapeutically effective amount of a compound of formula (II) as defined above or a pharmaceutically acceptable salt or stereoisomer thereof. Preferably the disease or condition associated with an elevated calpain activity is selected from the group consisting of heart injury caused by infarction, ischemia with or without reperfusion; neurodegenerative disorders; malaria; diabetic nephropathy; neurotoxicity induced by HIV virus; cancer; and fibrotic diseases; more preferably selected from the group consisting of heart injury caused by infarction, ischemia with or without reperfusion, still more preferably remodeling after myocardial infarction.

In particular embodiments, the disease or condition is selected from the group consisting of heart injury caused by infarction, ischemia with or without reperfusion; neurodegenerative disorders; malaria; diabetic nephropathy; neurotoxicity induced by HIV virus; and cancer.

In other particular embodiments, the disease or condition is heart injury caused by infarction, ischemia with or without reperfusion, preferably remodeling after myocardial infarction.

In other particular embodiments, the neurodegenerative disorder is selected from the group consisting of Alzheimer's disease, Parkinson disease, multiple sclerosis, acute autoimmune encephalitis, and Creutzfeldt-Jakob disease.

In other particular embodiments, the cancer is selected from the group consisting of breast cancer, colorectal cancer and leukaemia.

In other particular embodiments, the fibrotic disease is selected from the group consisting of cardiac fibrosis, lung fibrosis, liver fibrosis, renal fibrosis and retroperitoneal fibrosis.

Process for the Preparation of Compounds of Formulae (I) and (II)

The compounds of formula (I) and (II), preferably wherein $R_3$ is a cycloalkyl group, may be prepared starting from the N-substituted 3-amino-2-hydroxy-amide hydrochlorides of formula (VIII) following the synthetic scheme shown below:

In a first step the protected aminoacid of formula (VII), HOBt (hydroxybenzotriazol), EDC (1-ethyl-3-(3-dimethylaminopropyl)carbodiimide) and the N-substituted 3-amino-2-hydroxy-amide hydrochlorides of formula (VIII) are dissolved in a solvent such as dichloromethane (DCM). DIPEA (N,N-diisopropylethylamine) is then added and the mixture is left to react to yield the compound of formula (VI). Other amide coupling agents are equally effective such as HATU (1-[bis(dimethylamino)methylene]-1H-1,2,3-triazolo[4,5-b]pyridinium 3-oxide hexafluorophosphate) in the presence of DIPEA in dimethylformamide (DMF) or T3P (propylphosphonic anhydride) in the presence of $NEt_3$ in DMF. The compound of formula (VI) was reacted in a solvent such as 1,4-dioxane with a strong acid such as hydrochloric acid or in DCM and treated with trifluoroacetic acid (TFA) to yield the compound of formula (V). The compound of formula (III), HOBt, EDC and the compound of formula (V) are dissolved in a solvent such as DCM. DIPEA is then added and the mixture is left to react to yield the compound of formula (IV). Other amide coupling agents are equally effective such as HATU in the presence of DIPEA in DMF or T3P in the presence of $NEt_3$ in DMF. Finally, the compound of formula (IV) is dissolved in solvents such as DCM, DMF or a mixture of them and Dess-Martin periodinane is added to yield the compound of formula (I). Other oxidants such as DCC (N,N'-dicyclohexylcarbodiimide) in DMSO (dimethylsulfoxide) are equally useful.

The N-substituted 3-amino-2-hydroxy-amide hydrochlorides of formula (VIII) may be obtained starting from the protected aminoaldehydes of formula (XIII) following the synthetic scheme shown below:

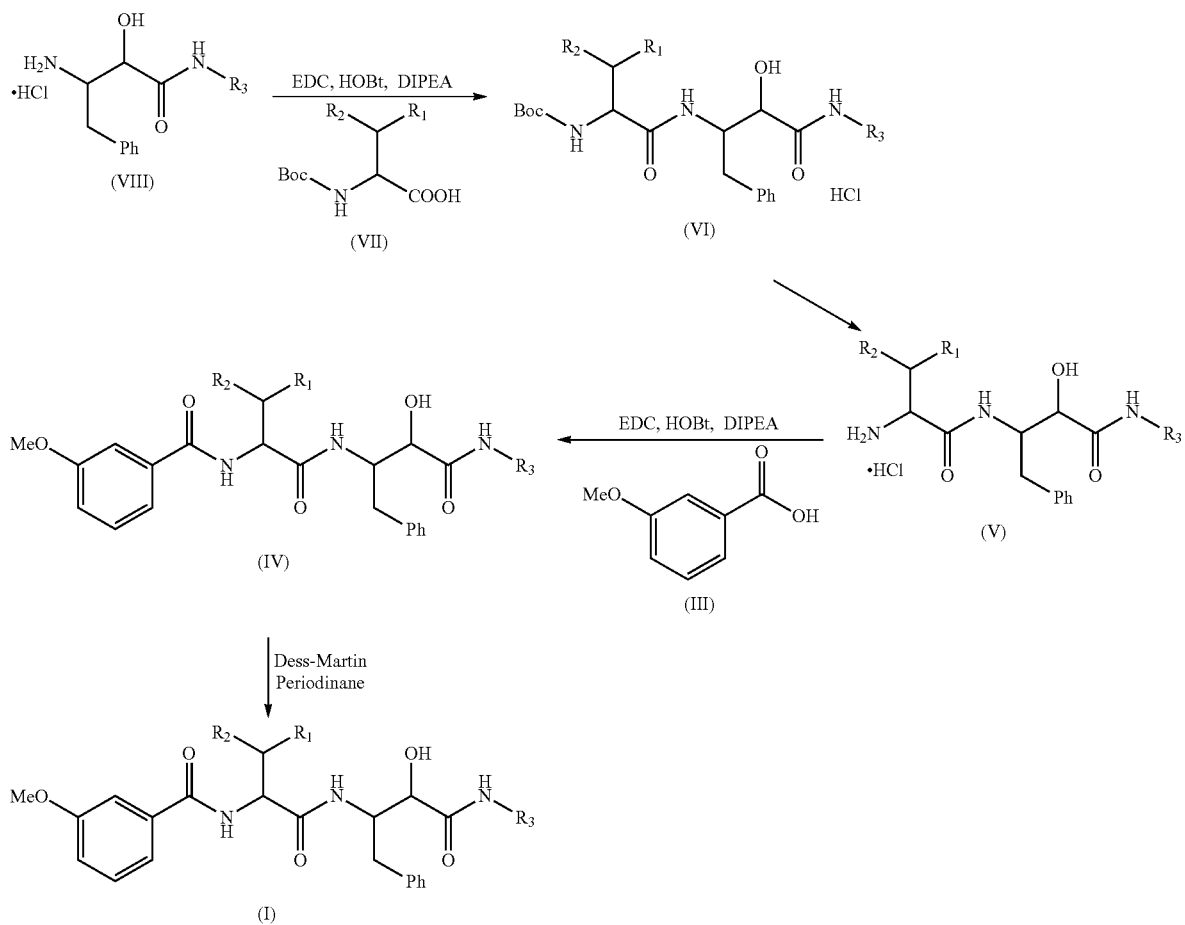

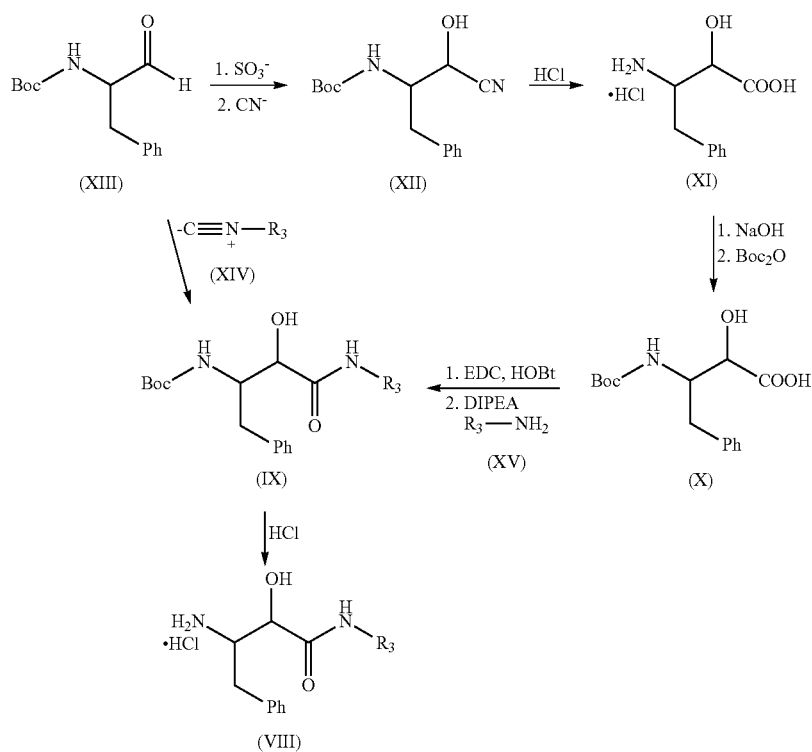

In a first step the protected aminoaldehydes of formula (XIII) are dissolved in a solvent such as 1,4-dioxane and sodium bisulfite is added followed by the addition of a potassium cyanide aqueous solution to yield the compound of formula (XII). The compound of formula (XII) is dissolved in a concentrated acid aqueous solution such as concentrated hydrochloric acid and refluxed to yield the compound of formula (XI). An aqueous solution of compound of formula (XI) is brought to alkaline pH (preferably in the range of 10-12) for example with sodium hydroxide and Boc$_2$O (di-tert-butyl dicarbonate) is added. After total conversion the mixture is acidified for example with KHSO$_4$ and the compound of formula (X) is extracted with a water-immiscible solvent such as ethyl acetate. The compound of formula (X), HOBt and EDC are dissolved in a solvent such as anhydrous DCM. DIPEA and the amine of formula (XV) are then added and the mixture is left to react for 8 to 24 hours react to yield the compound of formula (VIII). T3P or HATU can also be used instead of EDC and HOBt with good results. The compound of formula (IX) was reacted in a solvent such as 1,4-dioxane with a strong acid such as hydrochloric acid to yield the compound of formula (VIII).

In an alternative synthetic path which is also illustrated in the previous scheme, the protected aminoaldehydes of formula (XIII) are dissolved in a solvent such as anhydrous DCM and an acid such as acetic acid and an isocyanide compound of formula (XIV) are added and left to react in an inert atmosphere such as argon atmosphere at room temperature. Then solvent is removed and the resulting compound is extracted with ethyl acetate and washed with a saturated sodium bicarbonate aqueous solution. The product was then solved in a mixture of THF (tetrahydrofuran) and MeOH (methanol) and treated with a lithium hydroxide aqueous solution to yield the compound of formula (IX). Then, the compound of formula (IX) is reacted, as described above, in a solvent such as 1,4-dioxane with a strong acid such as hydrochloric acid to yield the compound of formula (VIII).

The compounds of formula (I) wherein R$_3$ is an alkoxy group may be prepared starting from the N-substituted 3-amino-2-hydroxy-amide hydrochlorides of formula (VIII) following the synthetic scheme shown below:

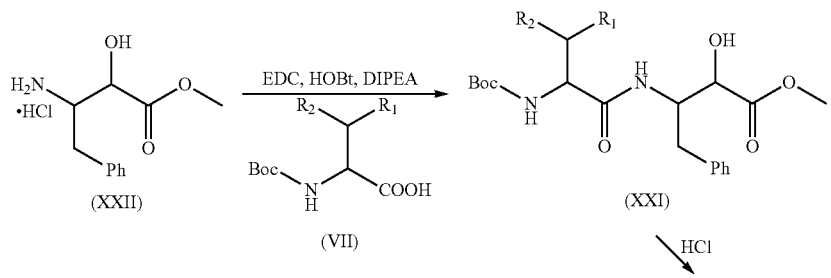

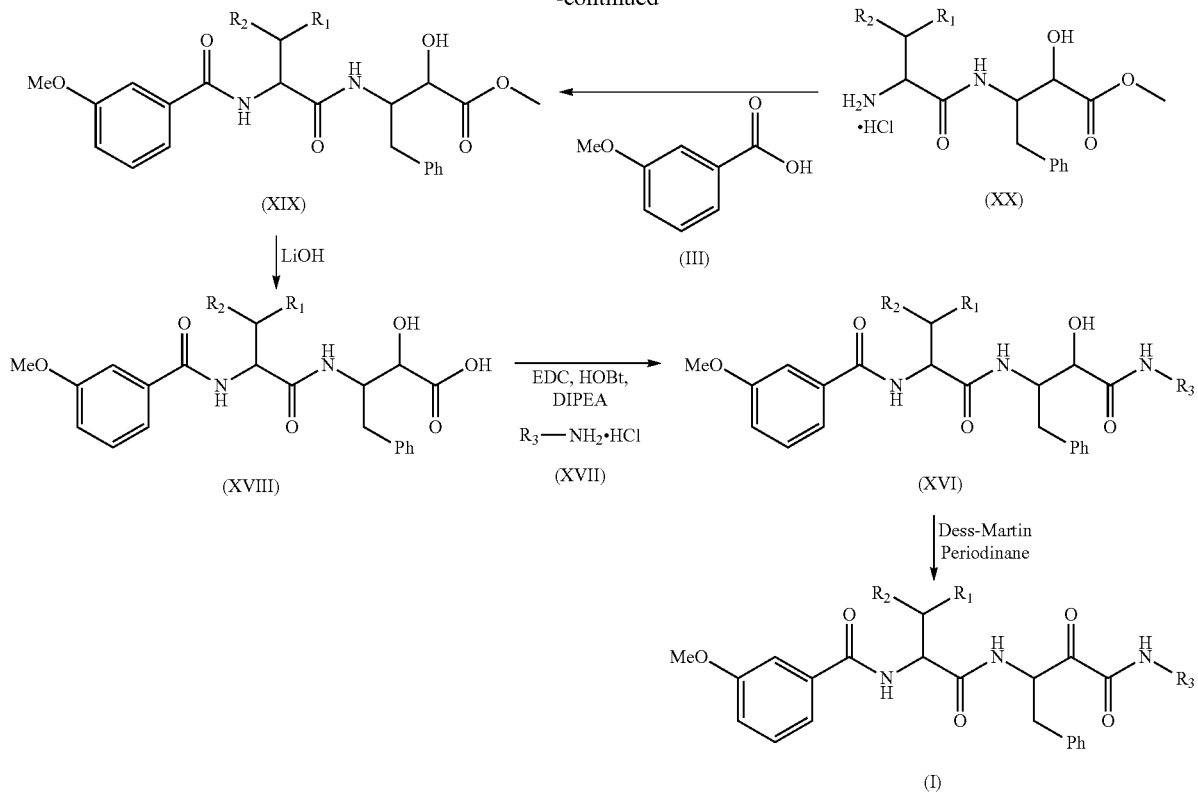

-continued

In a first step the protected aminoacid of formula (VII), HOBt, and the compound of formula (XXII) are dissolved in a solvent such as dichloromethane (DCM). DIPEA is then added and the mixture is left to react to yield the compound of formula (XXI). Other amide coupling agents are equally effective such as HATU in the presence of DIPEA in DMF or T3P in the presence of $NEt_3$ in DMF. The compound of formula (XXI) was reacted in a solvent such as 1,4-dioxane with a strong acid such as hydrochloric acid or in DCM and treated with trifluoroacetic acid (TFA) to yield the compound of formula (XX). The compound of formula (III), HOBt, EDC and the compound of formula (XX) are dissolved in a solvent such as DCM. DIPEA is then added and the mixture is left to react to yield the compound of formula (XIX). Other amide coupling agents are equally effective such as HATU in the presence of DIPEA in DMF or T3P in the presence of $NEt_3$ in DMF. The compound of formula (XIX) was then treated with LiOH in a mixture of THF/MeOH/water and subsequently treated with an aqueous acid solution such as HCl to give a compound of formula (XVIII). The compound of formula (XVII), HOBt, EDC and the compound of formula (XVIII) are dissolved in a solvent such as DCM. DIPEA is then added and the mixture is left to react to yield the compound of formula (XVI). Other amide coupling agents are equally effective such as HATU in the presence of DIPEA in DMF or T3P in the presence of $NEt_3$ in DMF. Finally, the compound of formula (XVI) is dissolved in solvents such as DCM, DMF or a mixture of them and Dess-Martin periodinane is added to yield the compound of formula (I). Other oxidants such as DCC (N,N'-dicyclohexylcarbodiimide) in DMSO (dimethylsulfoxide) are equally useful.

The compound of formula (XXII) may be obtained from a compound of formula (X), whose synthesis has been described above, by treatment with oxalyl chloride in methanol, as shown in the synthetic scheme below:

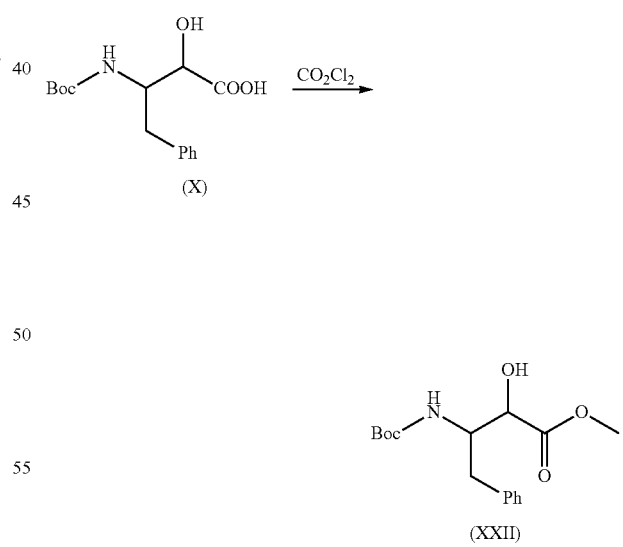

The starting compounds of formulae (XVII), (XIII), (XIV), (XV), (VII) and (III) are either commercially available or may be obtained by methods described in the literature.

The following examples are merely illustrative of certain embodiments of the invention and cannot be considered as restricting it in any way.

EXAMPLES

Abbreviations

The following abbreviations are used in the examples:
Boc: tert-butoxycarbonyl
conc: concentrate
Boc$_2$O: di-tert-butyl dicarbonate
DCM: dichloromethane
DIPEA: N,N-Diisopropylethylamine
DMSO: dimethylsulfoxide
EDC HCl: 1-ethyl-3-(3-dimethylaminopropyl)carbodiimide hydrochloride
EtOAc: ethyl acetate
HBTU: N,N,N',N'-Tetramethyl-O-(1H-benzotriazol-1-yl) uronium hexafluorophosphate
HCl: Hydrochloric Acid
HEPES: 4-(2-hydroxyethyl)-1-piperazineethanesulfonic acid
HOBt:hydroxybenzotriazol
LC-MS: liquid chromatography-mass spectrometry
Leu-OH: Leucine
MeOH: methanol
Min: minutes
Phe-OH: phenylalanine
Sat: saturated
T3P=Propylphosphonic Anhydride
TBME: tert-butyl methyl ether
THF: tetrahydrofuran
$t_R$: retention time
Val-OH: valine Materials and Methods LC-MS: The products of the examples were characterized using liquid chromatography coupled to mass spectroscopy (LC-MS). HPLC-MS analysis was carried out using the following procedure: In a an Alliance HT 2795 (Waters) chromatograph equipped with 2996 photodiode array detector and coupled to mass 3100 detector LC/MS. Separation was achieved using a XBridge C$_{18}$ column (50×4.6 mm, S-3.5 μm) and using mixtures of a 10 mM NH$_4$CO$_3$ aqueous solution of pH=9 (A) and acetonitrile (B) as eluents at 50° C. and 1.6 mL/min flow rate using the following eluting conditions: 5% to 100% B in 3.5 min. The detector was set at electrospray positive mode (ESI+) in the mass range of 100-700. Cone voltage 10 V. Source T: 120° C. Desolvation T: 350° C.

Reagents: 2-methoxybenzoic acid (Sigma Aldrich); 3-methoxybenzoic acid (Sigma Aldrich); 4-methoxybenzoic acid (Sigma Aldrich); Acetic acid (VWR); Boc-L-Phe-OH (Fluorochem); Boc-L-Leu-OH (Fluorochem); Boc-L-Val-OH (Fluorochem); cyclopropylamine (Sigma Aldrich); cyclopropylisocyanide (Fluorochem); Dess-Martin Periodinane 15% solution in DCM (Acros); EDC (Iris Biotech); HBTU (Iris Biotech); HCl 4N in 1,4-Dioxane (TCI Europe Organic Chem); HOBt (Carbosynth); LiOH.H$_2$O (Sigma Aldrich); Lithium aluminium hydride solution 1.0 M in tetrahydrofuran (Sigma Aldrich); N,O-dimethylhydroxylamine hydrochloride (Fluorochem); (S)-2-(Boc-amino)-3-cyclopropylpropanoic acid (Fluorochem).

Solvents: DCM (Scharlab); Ethanol (Panreac); EtOAc (Scharlab); Hexane (Scharlab); MeOH (Scharlab); TBME (SDS); THF (Panreac).

Synthesis of Intermediates

Intermediate 1: (S)-tert-butyl(1-(methoxy(methyl) amino)-1-oxo-3-phenylpropan-2-yl)carbamate

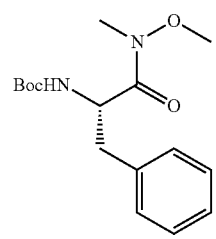 [SMILES: CON(C)C(=O)[C@H](Cc1ccccc1)NC(=O)OC(C)(C)C]

To a solution of Boc-L-Phe-OH (10.0 g, 37.7 mmol, 1.0 eq.) in DCM (150 ml), was added N,O-dimethylhydroxylamine hydrochloride (4.0 g, 41.1 mmol, 1.1 eq), HBTU (III) (15.7 g, 41.1 mmol, 1.1 eq) and DIPEA (20 ml, 113.0 mmol, 3.0 eq). The reaction mixture was stirred for 1 hour at room temperature. Volatiles were then removed under vacuum and the crude mixture extracted with EtOAc washed with a saturated solution of NaHCO$_3$ (2×200 mL). The crude material was purified by flash chromatography (ISCO Rf) using Hexane/EtOAc as eluents, from 0% to 40% in EtOAc, the product eluted at 35%. 11.6 g were obtained (37.7 mmol, 100% yield).

LC-MS: $t_R$=2.58 min; m/z=309

Intermediate 2: Synthesis of (S)-tert-butyl (1-oxo-3-phenylpropan-2-yl)carbamate Lithium aluminium hydride solution 1.0 M in tetrahydrofuran (37.7 ml, 37.7 mmol, 1.0 eq) was added to a solution of Intermediate 1 (11.6 g, 37.7 mmol, 1.0 eq.) in THF (250 ml) cooled to 0° C. The mixture was stirred overnight to room temperature. The reaction mixture was diluted with EtOAc and solvent was evaporated. The crude material was purified by silica gel chromatography using Hexane/EtOAc as solvents, from 0% to 60% in EtOAc, product eluted at 25%. 6.7 g of the desire product was obtained (26.9 mmol, 68% yield).

LC-MS: $t_R$=2.48 min; m/z=250

Intermediate 3: Synthesis of tert-butyl ((2S)-4-(cyclopropylamino)-3-hydroxy-4-oxo-1-phenylbutan-2-yl)carbamate

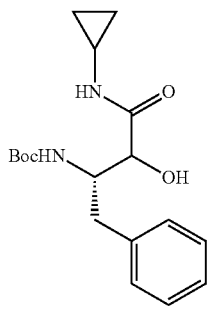 [SMILES: CC(C)(C)OC(=O)N[C@@H](Cc1ccccc1)C(O)C(=O)NC1CC1]

Acetic acid (0.35 ml, 8.0 mmol, 2.0 eq.) and cyclopropyl isocyanide (0.30 ml, 4.4 mmol, 1.1 eq.) were added to a solution of intermediate 2 (1.0 g, 4.0 mmol, 1.0 eq) in DCM (20 ml), and the mixture was stirred at rt. After 15 min, a mixture of THF/MeOH/H$_2$O (7/5/3) was added to the mixture and followed by LiOH.H$_2$O (0.67 g, 16.0 mmol, 4 eq.). After 15 min, the solvents were removed under vacuum. The product was extracted into EtOAc, and the solution washed with a sat. solution of NaHCO$_3$ and purified on flash chromatography (ISCO Rf) using Hexane/Hexane:Ethanol (8:2) as solvents, from 0% to 50% in Hexane:Ethanol (8:2), product eluted at 25%. 0.31 g of product was obtained (23% yield).

LC-MS: $t_R$=2.32 min; m/z=335

Intermediate 4: Synthesis of (3S)-3-amino-N-cyclopropyl-2-hydroxy-4-phenylbutanamide hydrochloride

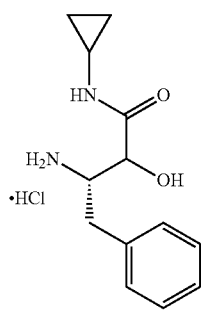 [SMILES: Cl ; N[C@@H](Cc1ccccc1)C(O)C(=O)NC1CC1]

A solution of HCl 4 N in 1,4-dioxane (1 ml, 4.1 mmol, 4 eq.) was added to intermediate 3 (0.31 g, 0.9 mmol, 1.0 eq.). The mixture was stirred at room temperature for 1 h and then evaporated to dryness. The product was used for the next step without further purification.

LC-MS: $t_R$=1.50 min; m/z=235

Intermediate 5: tert-butyl ((2S)-1-(((2S)-4-(cyclopropylamino)-3-hydroxy-4-oxo-1-phenylbutan-2-yl)amino)-4-methyl-1-oxopentan-2-yl)carbamate

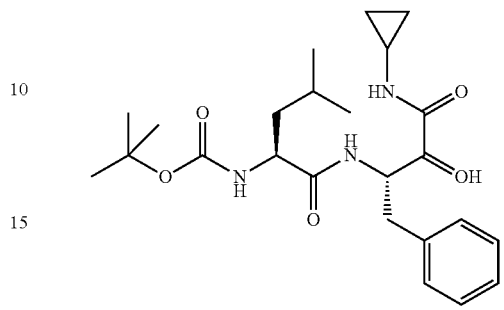

A solution of intermediate 4 (251 mg, 0.9 mmol, 1.0 eq.) and DIPEA (0.6 ml, 3.7 mmol, 4 eq.) in DCM (5 mL) was added to a solution of Boc-L-Leu-OH (300 mg, 1.2 mmol, 1.2 eq.), EDC (249 mg, 1.3 mmol, 1.5 eq.) and HOBt (199 mg, 1.3 mmol, 1.5 eq.) in DCM (5 mL). The reaction mixture was stirred for 1 hour at room temperature. The volatiles were removed under vacuum. The crude mixture was extracted with EtOAc and washed with a sat. solution of NaHCO$_3$ (2×10 mL) and purified by flash chromatography (ISCO Rf) using Hexane/TBME as eluents, from 0% to 80% in TBME, the product eluted at 60%. 298 mg of the product was obtained (0.7 mmol, 72% yield).

LC-MS (Method A): $t_R$=2.60 min; m/z=448

Intermediate 6: (2S)-2-amino-N-((2S)-4-(cyclopropylamino)-3-hydroxy-4-oxo-1-phenylbutan-2-yl)-4-methylpentanamide hydrochloride

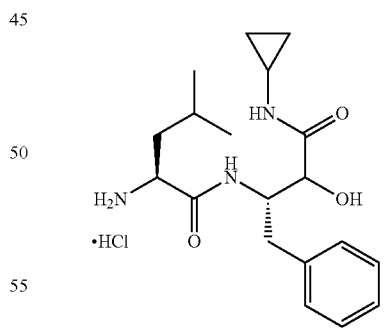

A solution of HCl (4 N) in 1,4-dioxane (3.3 ml, 13.2 mmol, 20 eq.) was added to intermediate 5 (298 mg, 0.6 mmol, 1.0 eq.). The mixture was stirred at room temperature for 1 h and then evaporated to dryness. The product was used for next step without further purification.

LC-MS: $t_R$=1.92-2.03 min; m/z=348

Intermediate 7: N-((2S)-1-(((2S)-4-(cyclopropylamino)-3-hydroxy-4-oxo-1-phenylbutan-2-yl)amino)-4-methyl-1-oxopentan-2-yl)-3-methoxybenzamide

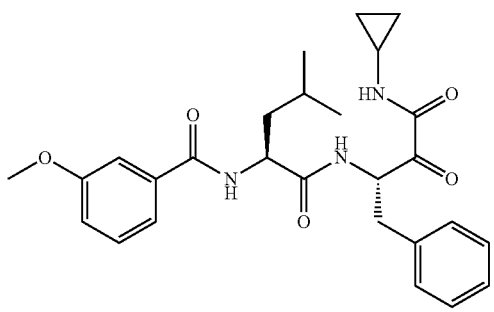 [SMILES: COc1cccc(C(=O)N[C@@H](CC(C)C)C(=O)N[C@@H](Cc2ccccc2)C(=O)C(=O)NC2CC2)c1]

A solution of intermediate 6 (115 mg, 0.3 mmol, 1.0 eq.) and DIPEA (231 µl, 1.3 mmol, 4.0 eq.) in DCM (5 mL) was added to a solution of 3-methoxybenzoic acid (60.4 mg, 0.4 mmol, 1.2 eq.), EDC (108 mg, 0.6 mmol, 1.7 eq.) and HOBt (86 mg, 0.6 mmol, 1.5 eq.) in DCM (4 mL). The reaction mixture was stirred for 1 hour at room temperature. The volatiles were removed under vacuum and the crude mixture was extracted with EtOAc and washed with a sat. solution of NaHCO$_3$ (2×20 mL). The material was purified by flash chromatography (ISCO Rf) using Hexane/Hexane:Ethanol (8:2) as eluents, from 0% to 60% in Hexane:Ethanol (8:2), product eluted at 40%. 100 mg product was obtained (0.2 mmol, 100%).

LC-MS: $t_R$=2.47 min; m/z=482

Intermediate 8: Synthesis of tert-butyl ((2S)-1-((4-(cyclopropylamino)-3-hydroxy-4-oxo-1-phenylbutan-2-yl)amino)-3-methyl-1-oxobutan-2-yl)carbamate

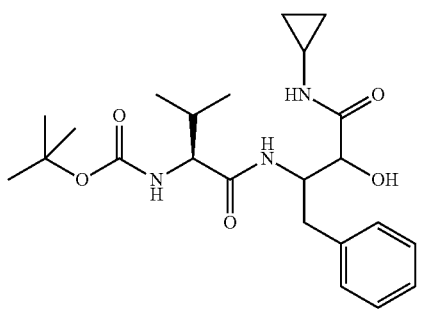 [SMILES: CC(C)[C@H](NC(=O)OC(C)(C)C)C(=O)NC(Cc1ccccc1)C(O)C(=O)NC1CC1]

A solution of intermediate 4 (1.06 g, 3.91 mmol, 1.0 eq.) and DIPEA (2.74 ml, 15.66 mmol, 4 eq.) in DCM (5 mL) was added to a solution of Boc-L-Val-OH (1.28 g, 5.87 mmol, 1.5 eq.), EDC (1.13 g, 5.87 mmol, 1.5 eq.) and HOBt (0.9 g, 5.87 mmol, 1.5 eq.) in DCM (5 mL). The reaction mixture was stirred for 45 minutes at room temperature and then the volatiles were removed under vacuum. The crude mixture was extracted with EtOAc and washed with a sat. solution of NaHCO$_3$. The crude material was purified by flash chromatography (ISCO Rf) using DCM/DCM:Methanol (8:2) as eluents, from 0% to 50% in DCM:Methanol (8:2), product eluted at 15%. 600 mg of product was obtained (1.384 mmol, 35% yield).

LC-MS: $t_R$=2.47 min; m/z=434

Intermediate 9: Synthesis of 3-((S)-2-amino-3-methylbutanamido)-N-cyclopropyl-2-hydroxy-4-phenylbutanamide hydrochloride

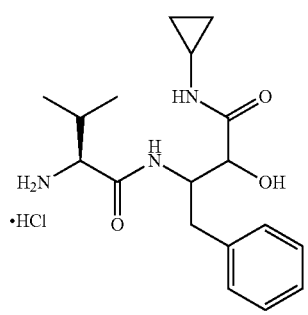 [SMILES: Cl ; CC(C)[C@H](N)C(=O)NC(Cc1ccccc1)C(O)C(=O)NC1CC1]

A solution of HCl 4 N in 1,4-dioxane (6.9 ml, 27.7 mmol, 20 eq.) was added to intermediate 8 (600 mg, 1.384 mmol, 1.0 eq.). The mixture was stirred at room temperature for 1 h and then evaporated to dryness. The product was used for next step without further purification.

LC-MS: $t_R$=1.77-1.88 min; m/z=334

Intermediate 10: Synthesis of N-((2S)-1-((4-(cyclopropylamino)-3-hydroxy-4-oxo-1-phenylbutan-2-yl)amino)-3-methyl-1-oxobutan-2-yl)-3-methoxybenzamide

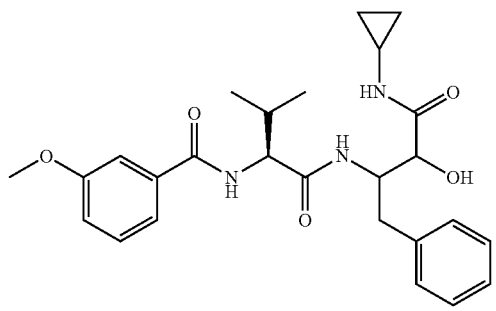 [SMILES: COc1cccc(C(=O)N[C@H](C(=O)NC(Cc2ccccc2)C(O)C(=O)NC2CC2)C(C)C)c1]

A solution of intermediate 9 (461 mg, 0.3 mmol, 1.0 eq.) and DIPEA (0.97 ml, 5.53 mmol, 4.0 eq.) in DCM (9 mL) was added to a solution of 3-methoxybenzoic acid (316 mg, 2.07 mmol, 1.5 eq.), EDC (398 mg, 2.07 mmol, 1.5 eq.) and HOBt (318 mg, 2.07 mmol, 1.5 eq.) in DCM (9 mL). The reaction mixture was stirred for 1 hour at room temperature and then the volatiles were removed under vacuum. The crude mixture was extracted with EtOAc and washed with a sat. solution of NaHCO$_3$. The crude material was purified by flash chromatography (ISCO Rf) using DCM/DCM:Methanol (8:2) as eluents, from 0% to 20% in DCM:Methanol (8:2), product eluted at 15%. 470 mg of product was obtained (1 mmol, 73%).

LC-MS: $t_R$=2.32 min; m/z=468

Intermediate 11: Synthesis of tert-butyl ((2S)-3-cyclopropyl-1-((4-(cyclopropylamino)-3-hydroxy-4-oxo-1-phenylbutan-2-yl)amino)-1-oxopropan-2-Yl)carbamate

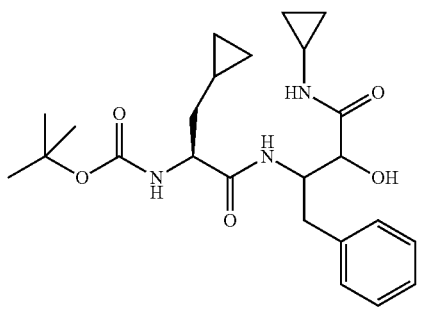 [SMILES: CC(C)(C)OC(=O)N[C@@H](CC1CC1)C(=O)NC(Cc1ccccc1)C(O)C(=O)NC1CC1]

A solution of intermediate 4 (530 mg, 1.96 mmol, 1.0 eq.) and DIPEA (1.37 ml, 7.83 mmol, 4 eq.) in DCM (3 mL) was added to a solution of (S)-2-(Boc-amino)-3-cyclopropylpropanoic acid (673 mg, 2.94 mmol, 1.5 eq.), EDC (563 mg, 2.94 mmol, 1.5 eq.) and HOBt (450 mg, 2.94 mmol, 1.5 eq.) in DCM (2 mL). The reaction mixture was stirred for one and a half hours at room temperature. The volatiles were removed under vacuum and the crude mixture was extracted with EtOAc and washed with a sat. solution of NaHCO$_3$. The crude mixture was purified on flash chromatography (ISCO Rf) using DCM/DCM:Methanol (8:2) as eluents, from 0% to 20% in DCM:Methanol (8:2), product eluted at 12%. 430 mg of product was obtained (0.96 mmol, 49% yield).

LC-MS: $t_R$=2.5 min; m/z=446

Intermediate 12: Synthesis of 3-((S)-2-amino-3-cyclopropylpropanamido)-N-cyclopropyl-2-hydroxy-4-phenylbutanamide hydrochloride

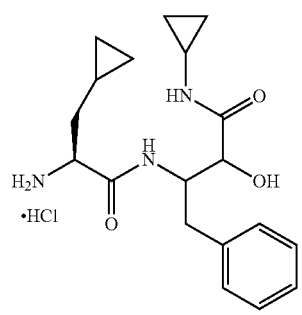 [SMILES: Cl ; N[C@@H](CC1CC1)C(=O)NC(Cc1ccccc1)C(O)C(=O)NC1CC1]

A solution of HCl 4 N in 1,4-Dioxane (4.83 ml, 19.3 mmol, 20 eq.) was added to Intermediate 11 (430 mg, 0.96 mmol, 1.0 eq.). The mixture was stirred at room temperature for 1 h and then vaporated to dryness. The product was used for next step without further purification.

LC-MS (Method A): $t_R$=1.82-1.92 min; m/z=346

Intermediate 13: Synthesis of N-((2S)-3-cyclopropyl-1-((4-(cyclopropylamino)-3-hydroxy-4-oxo-1-phenylbutan-2-yl)amino)-1-oxopropan-2-yl)-3-methoxybenzamide

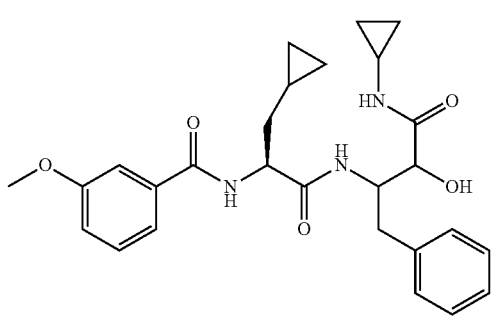 [SMILES: COc1cccc(C(=O)N[C@@H](CC2CC2)C(=O)NC(Cc2ccccc2)C(O)C(=O)NC2CC2)c1]

A solution of intermediate 12 (333 mg, 0.3 mmol, 1.0 eq.) and DIPEA (0.67 ml, 3.86 mmol, 4.0 eq.) in DCM (6 mL) was added to a solution of 3-methoxybenzoic acid (220 mg, 1.45 mmol, 1.5 eq.), EDC (277 mg, 1.45 mmol, 1.5 eq.) and HOBt (221 mg, 1.45 mmol, 1.5 eq.) in DCM (6 mL). The reaction mixture was stirred for 1 hour at room temperature and then the volatiles were removed under vacuum. The crude mixture was extracted with EtOAc and washed with a sat. solution of NaHCO$_3$. The crude material was purified on flash chromatography (ISCO Rf) using DCM/DCM:Methanol (8:2) as eluents, from 0% to 50% in DCM:Methanol (8:2), product eluted at 38%. 440 mg of product was obtained (0.88 mmol, 91%).

LC-MS: $t_R$=2.37 min; m/z=480

Intermediate 14: Synthesis of tert-butyl ((2S)-1-cyano-1-hydroxy-3-phenylpropan-2-yl)carbamate

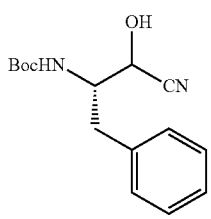 [SMILES: CC(C)(C)OC(=O)N[C@@H](Cc1ccccc1)C(O)C#N]

Sodium bisulfate (11.2 g, 107.0 mmol, 4 eq) was added to a solution of intermediate 2 (6.7 g, 26.9 mmol, 1.0 eq.) in 1,4-dioxane (150 ml) at 0° C. The reaction mixture was stirred at 0° C. for 10 minutes and potassium cyanide (7.0 g, 107.0 mmol, 4 eq) was added dissolved in water (45 mL). The reaction mixture was stirred overnight at room temperature. The organic solvent was evaporated, water and EtOAc were added and the layers separated. The combined organic layers were washed with sat. aq. NaHCO$_3$, dried and concentrated under reduced pressure. 7.0 g of product was obtained (23.5 mmol, 94% yield).

LC-MS: $t_R$=2.83 min; m/z=277

Intermediate 15: Synthesis of (3S)-3-((tert-butoxycarbonyl)amino)-2-hydroxy-4-phenylbutanoic acid

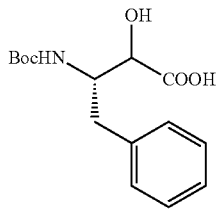 [SMILES: CC(C)(C)OC(=O)N[C@@H](Cc1ccccc1)C(O)C(=O)O]

Intermediate 14 (6.5 g, 23.5 mmol, 1.0 eq.) was dissolved in 20 ml of conc. HCl solution and refluxed for 1 hour. Then, the crude mixture was cooled and washed with DCM. NaOH 10 N was added to the aqueous layer until pH 11, and washed with DCM. Boc$_2$O (5.6 g, 25.8 mmol, 1.1 eq) was added to the aqueous layer. The mixture was stirred at room temperature overnight. After total conversion was achieved, the mixture was acidified with KHSO$_4$ to pH 2 and extracted with EtOAc. The organic layer was evaporated and the product was used for next step without further purification. 5.1 g was obtained (17.2 mmol, 73% yield 2 steps).

LC-MS: $t_R$=1.62 min; m/z=296

Intermediate 16: Synthesis of (3S)-methyl 3-amino-2-hydroxy-4-phenylbutanoate hydrochloride

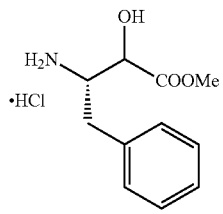 [SMILES: Cl ; COC(=O)C(O)[C@@H](N)Cc1ccccc1]

Oxalyl chloride (6 ml, 69.9 mmol, 4.0 eq.) was added slowly to a solution of intermediate 15 (5.1 g, 17.26 mmol, 1.0 eq.) in MeOH (300 ml) at 0° C. The mixture was stirred overnight at room temperature. The crude mixture was evaporated and then coevaporated with MeOH and the product was used for next step without further purification. 4.2 g was obtained (17.26 mmol, Quantitative yield).

LC-MS: $t_R$=1.58-1.65 min; m/z=210

Intermediate 17: Synthesis of methyl 3-((S)-2-((tert-butoxycarbonyl)amino)-3-cyclopropylpropanamido)-2-hydroxy-4-phenylbutanoate

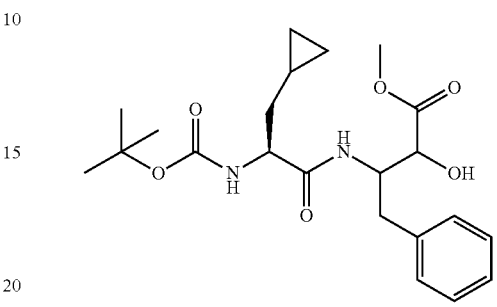

A solution of intermediate 16 (3 g, 12.21 mmol, 1.0 eq.) and DIPEA (8.53 ml, 48.8 mmol, 4 eq.) in DCM (15 mL) was added to a solution of (S)-2-(Boc-amino)-3-cyclopropylpropanoic acid (2.8 g, 12.21 mmol, 1 eq.), EDC (3.51 g, 18.31 mmol, 1.5 eq.) and HOBt (2.8 g, 18.31 mmol, 1.5 eq.) in DCM (10 mL). The reaction mixture was stirred for 1 hour at room temperature. The volatiles were removed under vacuum. The crude mixture was extracted with EtOAc and washed with a sat. solution of NaHCO$_3$. The crude product was purified on flash chromatography (Biotage) using DCM/DCM:Methanol (8:2) as eluents, from 0% to 30% in DCM:Methanol (8:2), product eluted at 20%. 2.2 g of product was obtained (5.23 mmol, 43% yield).

LC-MS: $t_R$=2.64 min; m/z=421

Intermediate 18: Synthesis of methyl 3-((S)-2-amino-3-cyclopropylpropanamido)-2-hydroxy-4-phenylbutanoate hydrochloride

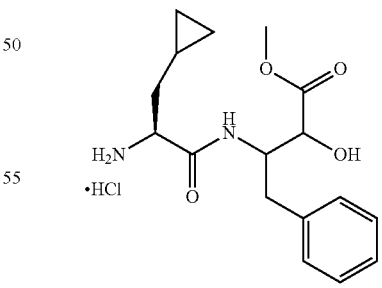

A solution of HCl 4 N in 1,4-dioxane (26.2 ml, 105 mmol, 20 eq.) was added to intermediate 17 (2.2 g, 5.23 mmol, 1.0 eq.). The mixture was stirred at room temperature for 1 h and then evaporated to dryness. The product was used for next step without further purification.

LC-MS: $t_R$=1.78 min; m/z=321

Intermediate 19: Synthesis of methyl 3-((S)-3-cyclopropyl-2-(3-methoxybenzamido)propanamido)-2-hydroxy-4-phenylbutanoate

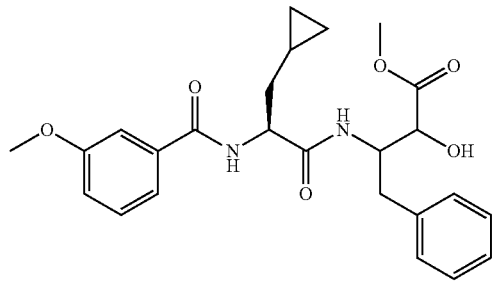 [SMILES: COC(=O)C(O)C(Cc1ccccc1)NC(=O)[C@H](CC1CC1)NC(=O)c1cccc(OC)c1]

A solution of intermediate 18 (1.87 g, 5.23 mmol, 1.0 eq.) and DIPEA (3.66 ml, 3.86 mmol, 4.0 eq.) in DCM (10 mL) was added to a solution of 3-methoxybenzoic acid (0.955 g, 6.28 mmol, 1.2 eq.), EDC (1.5 g, 7.85 mmol, 1.5 eq.) and HOBt (1.2 g, 7.85 mmol, 1.5 eq.) in DCM (10 mL). The reaction mixture was stirred for 1 hour at room temperature and then the volatiles were removed under vacuum. The crude mixture was extracted with EtOAc and washed with a sat. solution of NaHCO$_3$. The crude product was purified by flash chromatography (Biotage) using DCM/DCM:Methanol (8:2) as eluents, from 0% to 50% in DCM:Methanol (8:2), product eluted at 25%. 1 g of product was obtained (2.2 mmol, 42%).

LC-MS: $t_R$=2.47 min; m/z=455

Intermediate 20: Synthesis of 3-((S)-3-cyclopropyl-2-(3-methoxybenzamido)propanamido)-2-hydroxy-4-phenylbutanoic acid

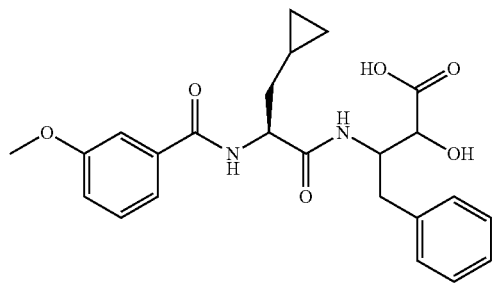 [SMILES: COc1cccc(C(=O)N[C@@H](CC2CC2)C(=O)NC(Cc2ccccc2)C(O)C(=O)O)c1]

LiOH.H$_2$O (111 mg, 2.64 mmol, 3.0 eq.) was added to a solution of intermediate 19 (400 mg, 0.88 mmol, 1.0 eq.) dissolved in 13.5 ml of a mixture THF/MeOH/H$_2$O (5/3/1). After total conversion was achieved, solvents were removed under vacuum. The crude material was dissolved in 1 M HCl and extracted with DCM until all Intermediate 20 had been extracted to the organic layer. The organic layers were evaporated to dryness. Intermediate 20 was used for next step without further purification.

LC-MS: $t_R$=1.85 min; m/z=441

Intermediate 21: Synthesis of N-((2S)-3-cyclopropyl-1-((3-hydroxy-4-(methoxyamino)-4-oxo-1-phenylbutan-2-yl)amino)-1-oxopropan-2-yl)-3-methoxybenzamide

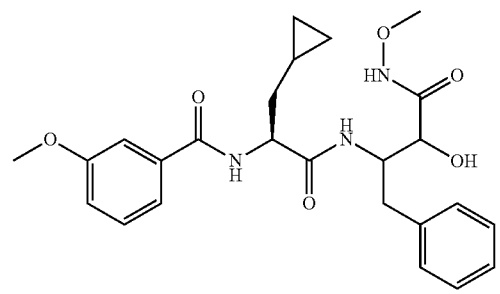 [SMILES: CONC(=O)C(O)C(Cc1ccccc1)NC(=O)[C@H](CC1CC1)NC(=O)c1cccc(OC)c1]

To a solution of Intermediate 20 (470 mg, 1.07 mmmol, 1.0 eq.) and O-methylhydroxylamine hydrochloride (134 mg, 1.6 mmmol, 1.5 eq.) in DCM (20 mL) was added EDC (307 mg, 1.6 mmol, 1.5 eq.) and HOBt (245 mg, 1.6 mmol, 1.5 eq.) and DIPEA (0.75 ml, 4.27 mmol, 4.0 eq.). The reaction mixture was stirred for 1 hour at room temperature. After this time 0.1 ml of DIPEA were added and the reaction stirred overnight at room temperature. 0.5 eq of both EDC and HOBt were added and stirring continued for 2 hours at room temperature. The volatiles were removed under vacuum. The crude mixture was extracted with EtOAc and washed with a sat. solution of NaHCO$_3$ and an aqueous solution of citric acid 5%. The crude product was purified on flash chromatography (Biotage) using DCM/DCM:Methanol (8:2) as eluents, from 0% to 50% in DCM:Methanol (8:2), product eluted at 20%. 170 mg of product was obtained. (0.37 mmol, 35% yield).

LC-MS: $t_R$=2.18 min; m/z=470

Intermediate 22: N-((2S)-1-(((2S)-4-(cyclopropylamino)-3-hydroxy-4-oxo-1-phenylbutan-2-yl)amino)-4-methyl-1-oxopentan-2-yl)-4-methoxybenzamide

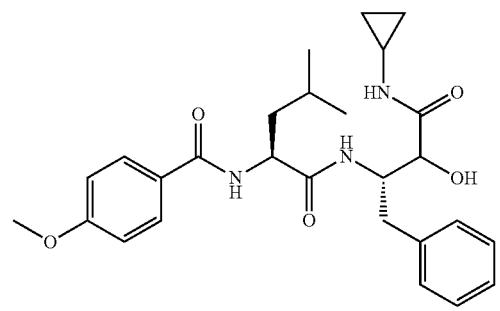 [SMILES: COc1ccc(C(=O)N[C@@H](CC(C)C)C(=O)N[C@@H](Cc2ccccc2)C(O)C(=O)NC2CC2)cc1]

A solution of intermediate 6 (200 mg, 0.6 mmol, 1.0 eq.) and DIPEA (392 μl, 2.3 mmol, 4.0 eq.) in DCM (6 mL) was added to a solution of 4-methoxybenzoic acid (105 mg, 0.7 mmol, 1.2 eq.), EDC (188 mg, 1.0 mmol, 1.7 eq.) and HOBt (150 mg, 1.0 mmol, 1.7 eq.) in DCM (6 mL). The reaction mixture was stirred for 1 hour at room temperature and the volatiles were removed under vacuum. The crude was extracted with EtOAc and washed with a sat. solution of NaHCO$_3$ (3×10 ml) and an aqueous solution of citric acid 5% (3×10 ml). The crude mixture was purified by flash chromatography (ISCO Rf) using Hexane/Hexane:Ethanol (8:2) as eluents, from 0% to 100% in Hexane:Ethanol (8:2), product eluted at 35%. 115 mg of product was obtained (0.2 mmol, 410%).

LC-MS: $t_R$=2.35 min; m/z=482

Intermediate 23: N-((2S)-1-(((2S)-4-(cyclopropylamino)-3-hydroxy-4-oxo-1-phenylbutan-2-yl)amino)-4-methyl-1-oxopentan-2-yl)-2-methoxybenzamide

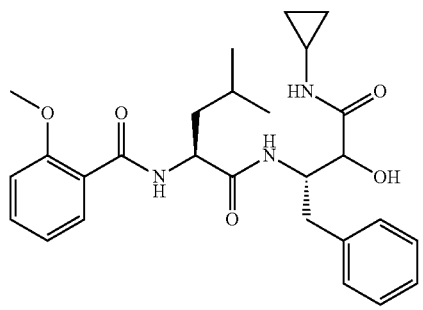 [SMILES: COc1ccccc1C(=O)N[C@@H](CC(C)C)C(=O)N[C@@H](Cc1ccccc1)C(O)C(=O)NC1CC1]

A solution of intermediate 6 (200 mg, 0.5 mmol, 1.0 eq.) and DIPEA (350 µl, 2.0 mmol, 4.0 eq.) in DCM (6 mL) was added to a solution of 2-methoxybenzoic acid (95 mg, 0.6 mmol, 1.2 eq.), EDC (169 mg, 0.9 mmol, 1.7 eq.) and HOBt (135 mg, 0.9 mmol, 1.7 eq.) in DCM (5 mL). The reaction mixture was stirred for 1 hour at room temperature and then the volatiles were removed under vacuum. The crude mixture was extracted with EtOAc and washed with a sat. solution of NaHCO$_3$ (3×10 ml) and an aqueous solution of citric acid 5% (3×10 ml). The crude product was purified on flash chromatography (ISCO Rf) using Hexane/Hexane:Ethanol (8:2) as eluents, from 0% to 100% in Hexane:Ethanol (8:2), product eluted at 35%. 250 mg were obtained (0.5 mmol, 100%).

LC-MS: $t_R$=2.47 min; m/z=482.

PREPARATION OF EXAMPLES AND COMPARATIVE EXAMPLES

Example 1: N-((S)-1-(((S)-4-(cyclopropylamino)-3,4-dioxo-1-phenylbutan-2-yl)amino)-4-methyl-1-oxopentan-2-yl)-3-methoxybenzamide

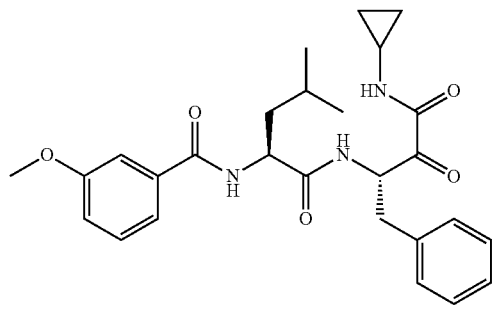 [SMILES: COc1cccc(C(=O)N[C@@H](CC(C)C)C(=O)N[C@@H](Cc2ccccc2)C(=O)C(=O)NC2CC2)c1]

5 µl of water were added to a Dess-Martin Periodinane 15% solution in DCM (640 µl, 0.3 mmol, 1.5 eq). Then the mixture was added to a solution of intermediate 7 (100 mg, 0.2 mmol, 1.0 mmol) in DCM (4 ml). The mixture was stirred for 15 minutes at room temperature and then the volatiles were removed under vacuum. The crude mixture was extracted with EtOAc and washed with a sat. solution of NaHCO$_3$ (2×10 mL). The crude product was purified by flash chromatography (ISCO Rf) using Hexane/Hexane:Ethanol (8:2) as solvents, from 0% to 60% in Hexane:Ethanol (8:2), product eluted at 30% in Hexane:Ethanol (8:2). 47.6 mg of product were obtained (0.1 mmol, 47% yield).

LC-MS: $t_R$=2.63 min; m/z=480

$^1$H NMR (400 MHz, DMSO-d6) δ 8.75 (dd, J=26.3, 5.1 Hz, 1H), 8.38 (dd, J=18.9, 8.1 Hz, 1H), 8.33 (d, J=7.7 Hz, 1H), 7.49-7.31 (m, 3H), 7.27-7.15 (m, 5H), 7.09 (m, 1H), 5.22-5.13 (m, 1H), 4.54 (m, 1H), 3.80 (s, 3H), 3.13 (m, 1H), 2.88-2.77 (m, 1H), 2.76-2.70 (m, 1H), 1.67-1.55 (m, 1H), 1.53-1.43 (m, 1H), 1.29 (m, 1H), 0.91-0.78 (m, 6H), 0.65 (m, 2H), 0.61-0.53 (m, 2H).

Example 2: Synthesis of N-((S)-1-((4-(cyclopropylamino)-3,4-dioxo-1-phenylbutan-2-yl)amino)-3-methyl-1-oxobutan-2-yl)-3-methoxybenzamide

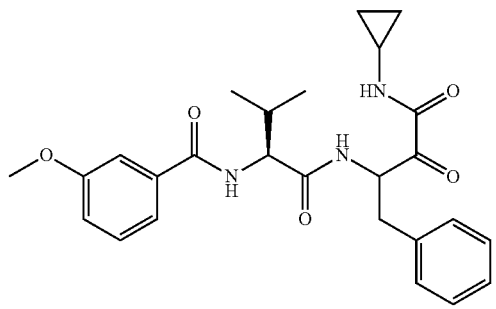 [SMILES: COc1cccc(C(=O)N[C@H](C(=O)NC(Cc2ccccc2)C(=O)C(=O)NC2CC2)C(C)C)c1]

Dess-Martin Periodinane 15% solution in DCM (3.13 ml, 1.51 mmol, 1.5 eq) was added to a solution of intermediate 10 (470 mg, 1 mmol, 1.0 eq) dissolved in a previously prepared solution in DCM (10 ml) and of water (5 µl). The mixture was stirred for 15 minutes at room temperature. After this time, 1.5 eq of Dess-Martin Periodinane 15% solution were added and mixture stirred for a further 15 minutes at room temperature. The volatiles were removed under vacuum and the crude mixture was extracted with EtOAc and washed with a 1 M solution of NaOH. The crude product was triturated using hexane and filtered. 352 mg of product was obtained (0.76 mmol, 76% yield).

LC-MS: $t_R$=2.52 min; m/z=466

$^1$H NMR (400 MHz, DMSO-d6) δ 0.61 (s, 2H), 0.61-0.68 (m, 2H), 0.73 (dd, J=23.0, 6.7 Hz, 3H), 0.87 (dd, J=6.7, 1.8 Hz, 3H), 1.92-2.10 (m, 1H), 2.68-2.85 (m, 2H), 3.07-3.18 (m, 1H), 3.81 (d, J=1.1 Hz, 3H), 4.32 (td, J=8.3, 5.6 Hz, 1H), 5.18-5.28 (m, 1H), 7.10 (dddd, J=8.0, 2.8, 1.9, 1.1 Hz, 1H), 7.15-7.25 (m, 5H), 7.34-7.46 (m, 3H), 8.15 (dd, J=11.8, 9.0 Hz, 1H), 8.45 (dd, J=14.4, 7.2 Hz, 1H), 8.76 (dd, J=21.8, 5.1 Hz, 1H).

Example 3: Synthesis of N-((S)-3-cyclopropyl-1-((4-(cyclopropylamino)-3,4-dioxo-1-phenylbutan-2-yl)amino)-1-oxopropan-2-yl)-3-methoxybenzamide

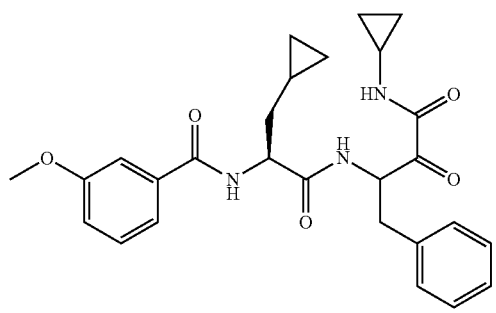 [SMILES: COc1cccc(C(=O)N[C@@H](CC2CC2)C(=O)NC(Cc2ccccc2)C(=O)C(=O)NC2CC2)c1]

Dess-Martin Periodinane 15% solution in DCM (2.73 ml, 1.31 mmol, 1.5 eq) was added to a solution of Intermediate 13 (420 mg, 0.88 mmol, 1.0 eq) dissolved in 8 ml of a previously prepared solution based in DCM (10 ml) and 5 µl of water. The mixture was stirred for 15 minutes at room temperature. After this time, 1.5 eq of Dess-Martin Periodinane 15% solution were added and mixture stirred for a further 15 minutes at room temperature. The volatiles were removed under vacuum and the crude mixture was extracted with EtOAc and washed with a 1 M solution of NaOH. The crude product was triturated using hexane and filtered. 274 mg of product was obtained (0.57 mmol, 65% yield).

LC-MS: $t_R$=2.57 min; m/z=478

$^1$H NMR (400 MHz, DMSO-$d_6$) δ −0.01-0.20 (m, 2H), 0.25-0.43 (m, 1H), 0.54-0.70 (m, 4H), 0.70-0.79 (m, 1H), 1.18-1.35 (m, 1H), 1.47-1.68 (m, 2H), 2.69-2.88 (m, 2H), 3.12 (td, J=13.5, 4.2 Hz, 1H), 3.80 (d, J=1.2 Hz, 3H), 4.55 (td, J=8.7, 5.1 Hz, 1H), 5.20 (dtd, J=9.0, 7.8, 4.1 Hz, 1H), 7.08-7.12 (m, 1H), 7.16-7.25 (m, 5H), 7.34-7.46 (m, 3H), 8.29-8.45 (m, 2H), 8.75 (dd, J=27.7, 5.1 Hz, 1H).

Example 4: Synthesis of N-((S)-3-cyclopropyl-1-((4-(methoxyamino)-3,4-dioxo-1-phenylbutan-2-yl)amino)-1-oxopropan-2-yl)-3-methoxybenzamide

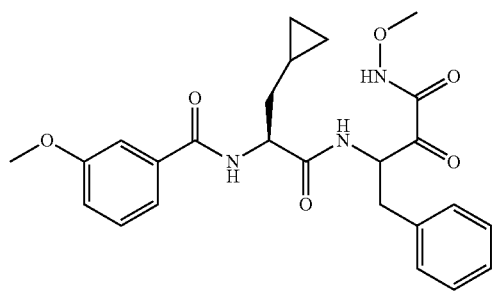 [SMILES: CONC(=O)C(=O)C(Cc1ccccc1)NC(=O)[C@H](CC1CC1)NC(=O)c1cccc(OC)c1]

Dess-Martin Periodinane 15% solution in DCM (0.827 ml, 0.4 mmol, 1.5 eq). was added in 4 portions to a solution of intermediate 21 (170 mg, 0.36 mmol, 1.0 eq) in DMSO (2.5 ml) stirring the mixture for 10 minutes between additions. The mixture was stirred for 2 hours at room temperature and then the volatiles were removed under vacuum. The crude mixture was extracted with EtOAc and washed with a 1 M solution of NaOH. The volatiles were evaporated and the crude mixture was purified on reverse phase chromatography (Biotage) using H$_2$O/Acetonitrile as solvents, from 0% to 100% in Acetonitrile, product eluted at 20%. 14.2 mg of product were obtained (0.03 mmol, 8% yield).

LC-MS: $t_R$=2.03 min; m/z=468

$^1$H NMR (400 MHz, DMSO-$d_6$) δ −0.04-0.23 (m, 1H), 0.34 (ddd, J=17.7, 9.1, 5.5 Hz, 1H), 1.43-1.68 (m, 1H), 2.52 (d, J=1.9 Hz, 1H), 2.67-2.83 (m, 1H), 3.10-3.22 (m, 2H), 3.65 (d, J=13.1 Hz, 2H), 3.79 (d, J=2.2 Hz, 3H), 4.53 (tt, J=9.0, 4.6 Hz, 1H), 5.32 (s, 1H), 6.95-7.33 (m, 6H), 7.33-7.46 (m, 3H), 8.09 (d, J=72.5 Hz, 1H), 8.34 (dd, J=26.3, 8.3 Hz, 1H).

Comparative Example 5: N-((S)-1-(((S)-4-(cyclopropylamino)-3,4-dioxo-1-phenylbutan-2-yl)amino)-4-methyl-1-oxopentan-2-yl)-4-methoxybenzamide

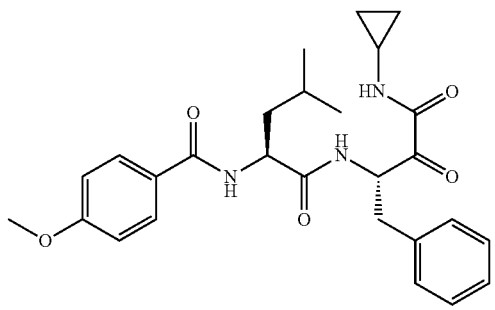 [SMILES: COc1ccc(C(=O)N[C@@H](CC(C)C)C(=O)N[C@@H](Cc2ccccc2)C(=O)C(=O)NC2CC2)cc1]

5 µL of water were added to Dess-Martin Periodinane 15% solution in DCM (744 µl, 0.3 mmol, 1.5 eq). Then the mixture was added to a solution of intermediate 22 (115 mg, 0.2 mmol, 1.0 eq.) in DCM (5 ml). The mixture was stirred for 15 minutes at room temperature. Volatiles were removed under vacuum. Crude was extracted with EtOAc and washed with a sat. solution of NaHCO$_3$ (2×10 mL). Crude was purified on flash chromatography (ISCO Rf) using Hexane/Hexane:Ethanol (8:2) as solvents, from 0% to 30% in Hexane:Ethanol (8:2), product eluted at 20%. 31.2 mg were obtained (0.2 mmol, 27%).

LC-MS: $t_R$=2.60 min; m/z=480

$^1$H NMR (400 MHz, DMSO-d6) δ 8.74 (dd, J=25.5, 5.1 Hz, 1H), 8.33 (dd, J=34.8, 7.4 Hz, 1H), 8.19 (dd, J=14.2, 8.4 Hz, 1H), 7.88-7.82 (m, 2H), 7.24-7.14 (m, 5H), 7.03-6.95 (m, 2H), 5.17 (m, 1H), 4.52 (m, 1H), 3.81 (s, 3H), 3.12 (m, 1H), 2.91-2.74 (m, 1H), 2.74-2.65 (m, 1H), 1.60 (m, 1H), 1.48 (m, 1H), 1.30 (m, 1H), 0.92-0.78 (m, 6H), 0.68-0.61 (m, 2H), 0.58 (m, 2H).

Comparative Example 6: N-((S)-1-(((S)-4-(cyclopropylamino)-3,4-dioxo-1-phenylbutan-2-yl)amino)-4-methyl-1-oxopentan-2-yl)-2-methoxybenzamide

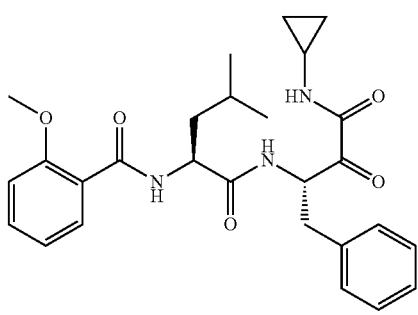 [SMILES: COc1ccccc1C(=O)N[C@@H](CC(C)C)C(=O)N[C@@H](Cc1ccccc1)C(=O)C(=O)NC1CC1]

5 µL of water were added to a Dess-Martin Periodinane 15% solution in DCM (1.6 ml, 0.7 mmol, 1.5 eq). Then the mixture was added to a solution of intermediate 23 (250 mg, 0.5 mmol, 1.0 eq.) in DCM (10 ml). The mixture was stirred for 15 minutes at room temperature. The volatiles were removed under vacuum and the crude mixture was extracted with EtOAc and washed with a sat. solution of NaHCO$_3$ (2×10 mL). The crude product was purified on flash chromatography (ISCO Rf) using Hexane/Hexane:Ethanol (8:2) as solvents, from 0% to 30% in Hexane:Ethanol (8:2), product eluted at 20%. 89.2 mg of product was obtained (0.2 mmol, 35%).

LC-MS: $t_R$=2.68 min; m/z=480

$^1$H NMR (400 MHz, DMSO-d6) δ 8.78 (dd, J=19.7, 5.1 Hz, 1H), 8.51 (dd, J=32.3, 7.5 Hz, 1H), 8.26 (dd, J=8.2, 6.1 Hz, 1H), 7.79 (m, 1H), 7.49 (m, 1H), 7.25-7.21 (m, 4H), 7.20-7.13 (m, 2H), 7.05 (m, 1H), 5.24-5.17 (m, 1H), 4.63-4.55 (m, 1H), 3.86 (s, 3H), 3.15 (m, 1H), 2.85-2.75 (m, 1H), 2.75-2.70 (m, 1H), 1.66-1.46 (m, 2H), 1.36 (m, 1H), 0.91-0.77 (m, 6H), 0.67-0.62 (m, 2H), 0.61-0.55 (m, 2H).

Biological Data

Assay for the Determination of the Capacity to Inhibit Calpain 1

Activity of Calpain 1 was measured by using Calpain-Glo Protease kit from Promega. Assays were run in 384-well black plates with clear bottom. 5 µl of compounds in a 10 mM HEPES and 1 mM EDTA aqueous solution were incubated with 15 µL of a solution of 16 ng/mL calpain 1 (Sigma Aldrich) for 2 minutes and then 20 µL of Calpain-Glo™ Reagent provided in the kit were added to each well. Luminescence elicited by calpain 1-induced substrate lysis was measured in a Hamamatsu FDSS 7000 reader and data was calculated from the maximal luminescence peak. Calpain inhibition was calculated from the formula:

% inhibition=(LT−LB)*100/(LC−LB);

wherein LT is the luminescence observed in the tested compound, LB is blank luminescence obtained from a well without calpain 1 and LC is the luminescence observed in control wells including calpain1 in the absence of inhibitor.

All compounds were tested using, at least, 6 concentrations to allow calculate the IC50 (concentration that inhibits the activity of calpain 1 by 50%).

Calpastatin and ALLN were included as control inhibitors in all the assays.

| Compound | Calpain 1 inhibitory activity IC$_{50}$ (nM) |
| --- | --- |
| Example 1 | 0.03 |
| Example 2 | 2.2 |
| Example 3 | 0.008 |
| Example 4 | 7.1 |
| Comp. Example 5 | 255 |
| Comp. Example 6 | 110 |

The invention claimed is:

1. A method for the treatment of a disease or condition associated with elevated calpain 1 activity selected from the group consisting of heart injury caused by infarction; ischemia with or without reperfusion; neurodegenerative disorders; malaria; diabetic nephropathy; neurotoxicity induced by HIV virus; cancer; and fibrotic diseases, the method comprising administering to a subject in need thereof a therapeutically effective amount of a calpain 1 inhibitor of formula (I):

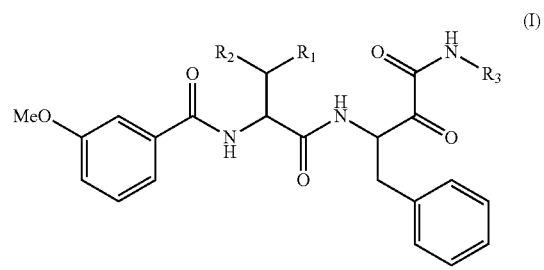

wherein
$R_1$ is selected from the group consisting of $C_1$-$C_6$ alkyl and $C_3$-$C_6$ cycloalkyl,
$R_2$ is selected from the group consisting of H and $C_1$-$C_6$ alkyl, and
$R_3$ is selected from the group consisting of $C_1$-$C_6$ alkoxy and $C_3$-$C_6$ cycloalkyl,
or a pharmaceutically acceptable salt or stereoisomer thereof
or a pharmaceutical composition comprising said compound and a pharmaceutically acceptable excipient.

2. The method according to claim 1, wherein
$R_1$ is selected from the group consisting of $C_1$-$C_3$ alkyl and $C_3$-$C_5$ cycloalkyl,
$R_2$ is selected from the group consisting of H and $C_1$-$C_3$ alkyl, and
$R_3$ is selected from the group consisting of $C_1$-$C_3$ alkoxy and $C_3$-$C_5$ cycloalkyl.

3. The method according to claim 1, wherein $R_1$ is selected from the group consisting of methyl, isopropyl and cyclopropyl.

4. The method according to claim 1, wherein $R_2$ is selected from the group consisting of H and methyl.

5. The method according to claim 1, wherein $R_3$ is selected from the group consisting of cyclopropyl and methoxy.

6. The method according to claim 1, wherein the compound of formula (I) is selected from the group consisting of:

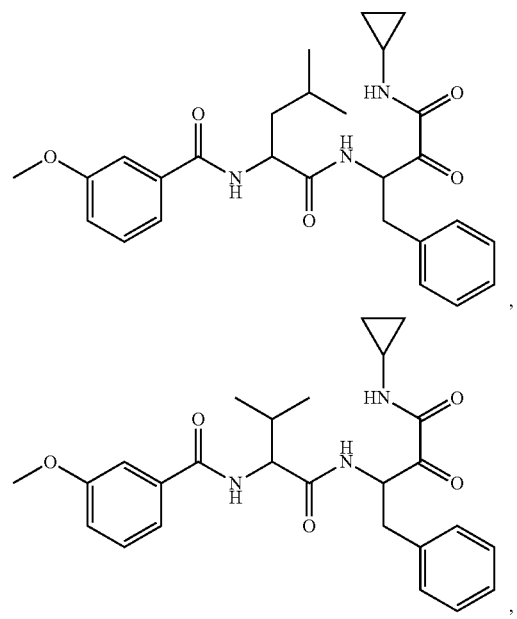

-continued

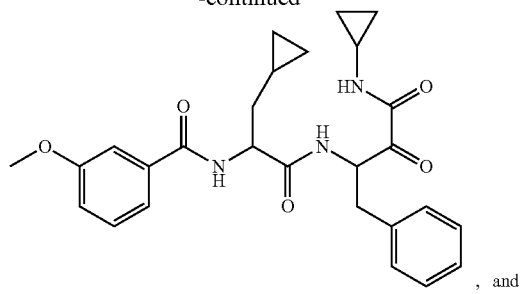

, and

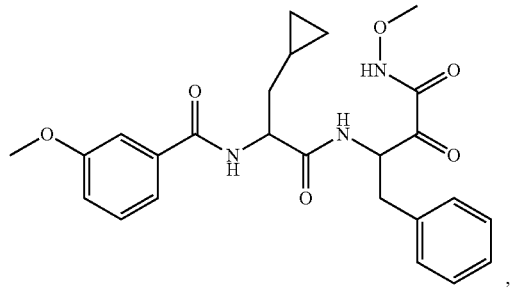

, or a stereoisomer or pharmaceutically acceptable salt thereof.

7. The method according to claim 1, wherein the compound of formula (I) is selected from the group consisting of:

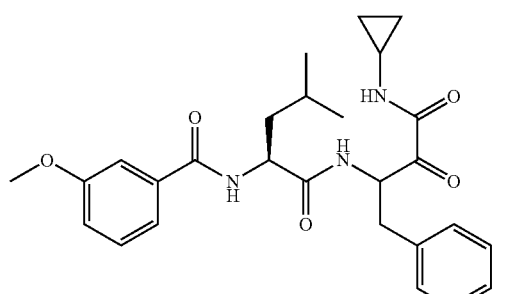

,

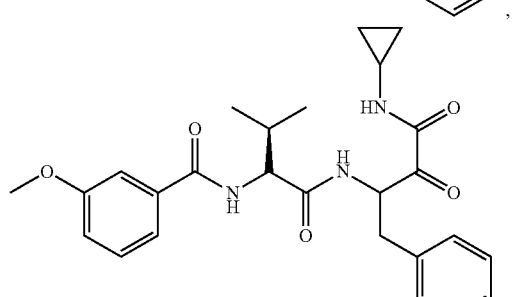

,

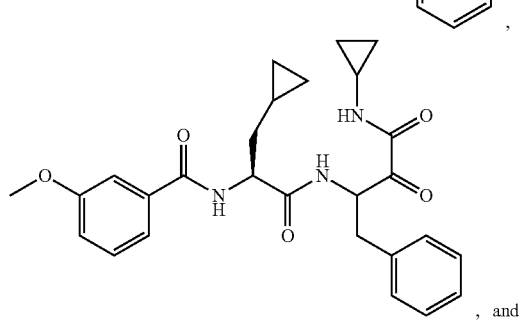

, and

-continued

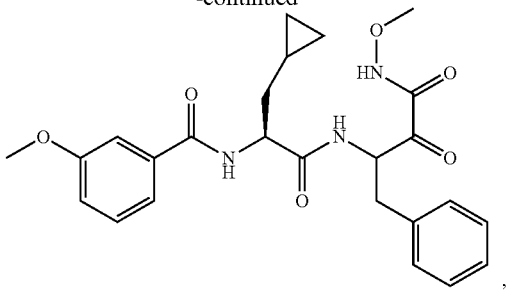

, or a stereoisomer or pharmaceutically acceptable salt thereof.

8. The method according to claim 1, wherein the compound of formula (I) is selected from the group consisting of:

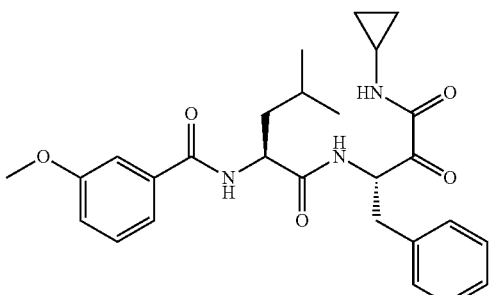

,

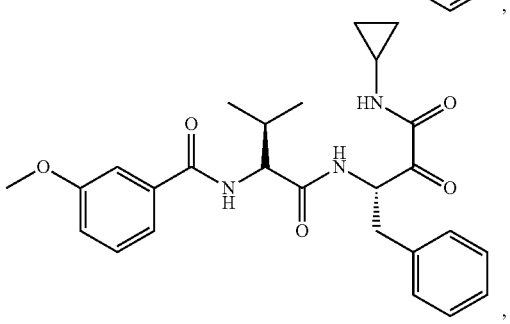

,

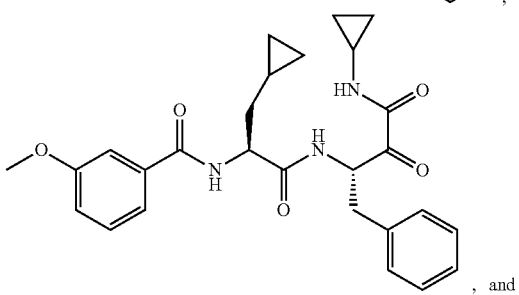

, and

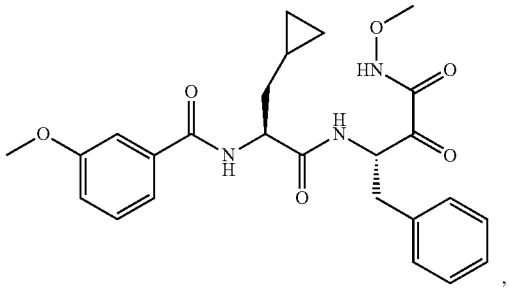

, or a pharmaceutically acceptable salt thereof.

9. The method according to claim 1, wherein the disease or condition is heart injury caused by infarction or ischemia with or without reperfusion.

10. The method according to claim 9, wherein the heart injury is remodeling after myocardial infarction.

11. The method according to claim 1, wherein the neurodegenerative disorder is selected from the group consisting of Alzheimer's disease, Parkinson disease, multiple sclerosis, acute autoimmune encephalitis, and Creutzfeldt-Jakob disease; and/or cancer is selected from the group consisting of breast cancer, colorectal cancer and leukaemia.

12. The method according to claim 1, wherein the fibrotic disease is selected from the group consisting of cardiac fibrosis, lung fibrosis, liver fibrosis, renal fibrosis and retroperitoneal fibrosis.

13. A compound of formula (II):

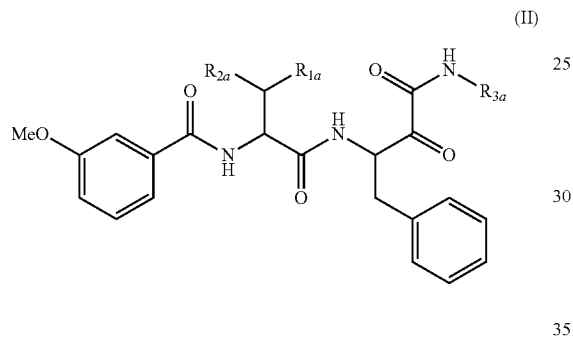

(II)

wherein $R_{1a}$ is selected from the group consisting of $C_1$-$C_6$ alkyl and $C_3$-$C_6$ cycloalkyl, $R_{2a}$ is selected from the group consisting of H and $C_1$-$C_6$ alkyl, and $R_{3a}$ is $C_3$-$C_6$ cycloalkyl, or a pharmaceutically acceptable salt or stereoisomer thereof.

14. The compound of formula (II) according to claim 13, wherein $R_{1a}$ is selected from the group consisting of $C_1$-$C_3$ alkyl and $C_3$-$C_{05}$ cycloalkyl, $R_{2a}$ is selected from the group consisting of H and $C_1$-$C_3$ alkyl, $R_{3a}$ is $C_3$-$C_5$ cycloalkyl.

15. The compound of formula (II) according to claim 13, wherein $R_{1a}$ is selected from the group consisting of methyl, isopropyl and cyclopropyl.

16. The compound of formula (II) according to claim 13, wherein $R_{2a}$ is selected from the group consisting of H and methyl.

17. The compound of formula (II) according to claim 13, wherein $R_{3a}$ is cyclopropyl.

18. The compound of formula (II) according to claim 13, which is selected from the group consisting of:

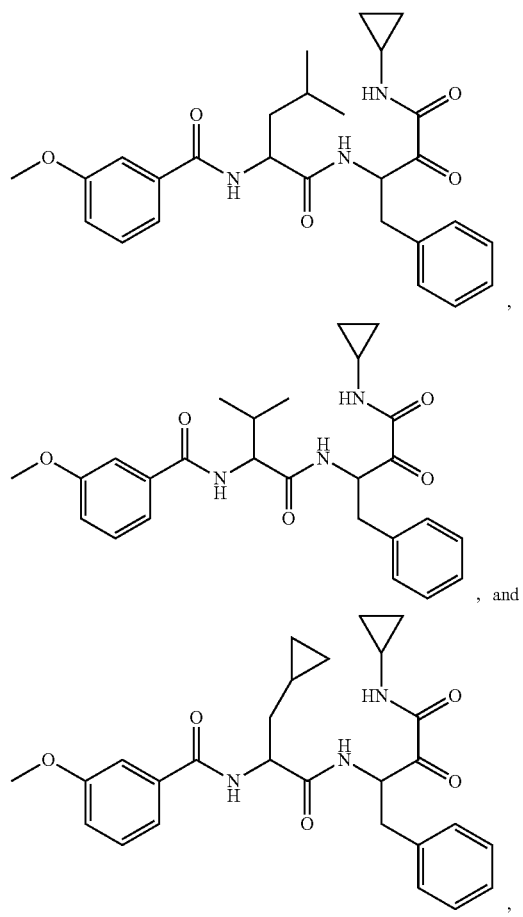

, and or a stereoisomer or pharmaceutically acceptable salt thereof.

19. The compound of formula (II) according to claim 13, which is selected from the group consisting of:

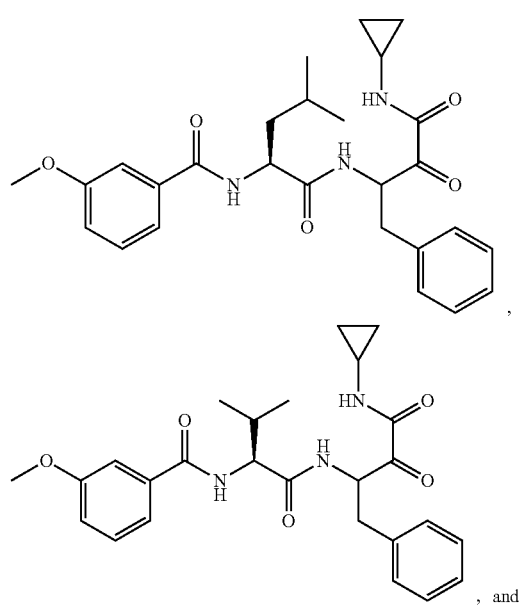

, and

-continued
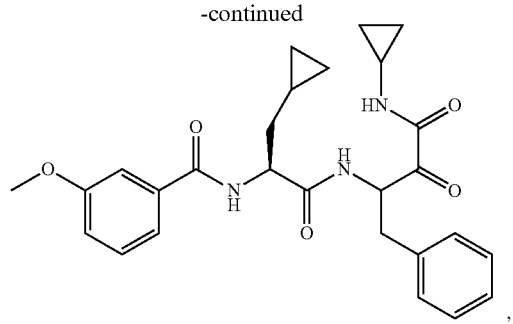
or a stereoisomer or pharmaceutically acceptable salt thereof.
20. The compound of formula (II) according to claim 13, which is selected from the group consisting of:
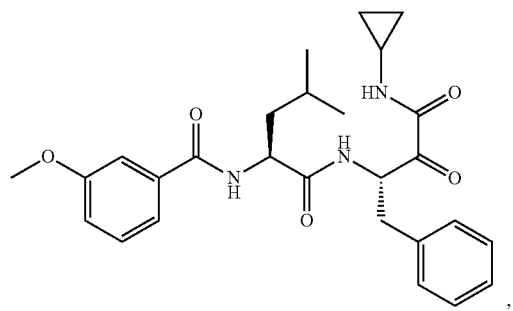
-continued
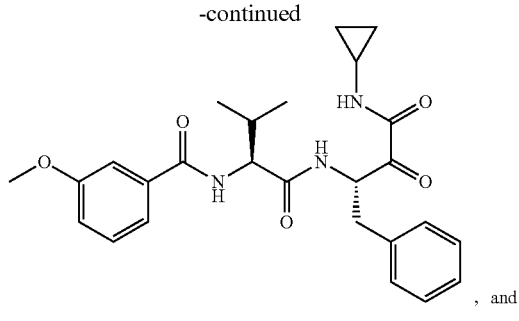
, and
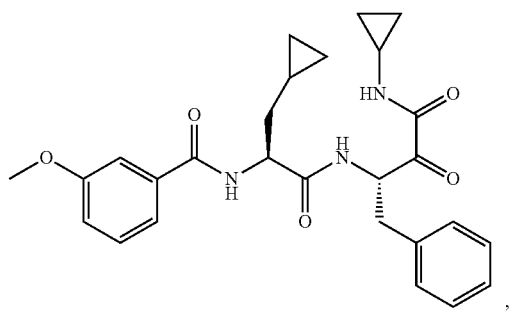
,
or a pharmaceutically acceptable salt thereof.
* * * * *